(12) United States Patent
Hamper et al.

(10) Patent No.: US 7,002,052 B2
(45) Date of Patent: Feb. 21, 2006

(54) INTEGRATED PROCESS FOR PRODUCING AN ALKENYL-SUBSTITUTED AROMATIC COMPOUND

(75) Inventors: Simon Hamper, Lake Jackson, TX (US); William M. Castor, Lake Jackson, TX (US); Richard A. Pierce, Lake Jackson, TX (US)

(73) Assignee: Dow Global Technologies Inc., Midland, MI (US)

( * ) Notice: Subject to any disclaimer, the term of this patent is extended or adjusted under 35 U.S.C. 154(b) by 760 days.

(21) Appl. No.: 10/181,106

(22) PCT Filed: Jan. 24, 2001

(86) PCT No.: PCT/US01/02673

§ 371 (c)(1),
(2), (4) Date: Jul. 11, 2002

(87) PCT Pub. No.: WO01/56960

PCT Pub. Date: Aug. 9, 2001

(65) Prior Publication Data

US 2003/0028059 A1    Feb. 6, 2003

Related U.S. Application Data

(60) Provisional application No. 60/179,690, filed on Feb. 2, 2000.

(51) Int. Cl.
*C07C 15/46* (2006.01)
*C07C 11/04* (2006.01)
*C07C 5/333* (2006.01)

(52) U.S. Cl. .................. 585/323; 585/314; 585/440; 585/444

(58) Field of Classification Search ............... 585/323, 585/314, 440, 444
See application file for complete search history.

(56) References Cited

U.S. PATENT DOCUMENTS

| 2,429,161 A | 10/1947 | Hudson |
| 3,888,762 A | 6/1975 | Gerhold |
| 4,229,604 A | 10/1980 | Tmenov et al. |

(Continued)

FOREIGN PATENT DOCUMENTS

EP    0 637 578    4/1996

(Continued)

OTHER PUBLICATIONS

Chemical Engineering Progress, vol. 47, No. 2, Feb. 1951 p. 95-101. "Moving Bed Recycle Catalytic Cracking Correlations" Meerker et al.

(Continued)

*Primary Examiner*—Elizabeth D. Wood (57) ABSTRACT

An integrated process of preparing a $C_{2-5}$ alkenyl-substituted aromatic compound using a $C_{6-12}$ aromatic compound and a $C_{2-5}$ alkane as raw materials. The process involves feeding a $C_{2-5}$ alkane, for example ethane, and a $C_{2-5}$ alkyl-substituted aromatic compound, for example ethylbenzene, to a dehydrogenation reactor for concurrent dehydrogenation to a $C_{2-5}$ alkene, for example ethylene, and a $C_{2-5}$ alkenyl-substituted aromatic compound, for example stryrene; separating the dehydrogenation effluent to recover a gaseous stream containing alkene, hydrogen, and alkane, and to recover the aromatics with high efficiency; feeding the gas stream and a $C_{6-12}$ aromatic compound to an alkylation reactor to obtain the corresponding $C_{2-5}$ alkyl-substituted aromatic compound, which is recycled to the dehydrogenation reactor; subjecting the alkylation unit vent stream containing alkane and hydrogen to a separation step to recover alkane, which is recycled to the dehydrogenation unit; hydrogen, which is recovered at 99% chemical grade purity and energy.

63 Claims, 2 Drawing Sheets

U.S. PATENT DOCUMENTS

| | | | |
|---|---|---|---|
| 4,502,947 A | 3/1985 | Haddad et al. | |
| 4,985,136 A | 1/1991 | Bartholic | |
| 5,248,411 A | 9/1993 | Chan | |
| 5,346,613 A | 9/1994 | Lomas et al. | |
| 5,430,211 A | 7/1995 | Pogue et al. | 585/323 |
| 5,451,313 A | 9/1995 | Wegerer et al. | |
| 5,455,010 A | 10/1995 | Lomas et al. | |
| 5,476,978 A | 12/1995 | Smith, Jr. et al. | 585/323 |
| 5,510,553 A | 4/1996 | Delorme et al. | |
| 5,597,537 A | 1/1997 | Wegerer et al. | |
| 5,756,872 A | 5/1998 | Smith, Jr. et al. | 585/449 |
| 5,858,207 A | 1/1999 | Lomas | |
| 5,965,012 A | 10/1999 | Lomas | |
| 6,010,618 A | 1/2000 | Lomas | |
| 6,031,143 A | 2/2000 | Buonomo et al. | |
| 6,113,776 A | 9/2000 | Upson | |
| 6,143,253 A | 11/2000 | Radcliffe et al. | |
| 6,183,699 B1 | 2/2001 | Lomas | |
| 2002/0183573 A1 | 12/2002 | Cocco et al. | |
| 2003/0028059 A1 | 2/2003 | Hamper et al. | |
| 2003/0196933 A1 | 10/2003 | Lomas et al. | |
| 2003/0223918 A1 | 12/2003 | Cammy et al. | |
| 2004/0064006 A1 | 4/2004 | Beech, Jr. et al. | |
| 2004/0082824 A1 | 4/2004 | Lattner | |
| 2004/0242945 A1 | 12/2004 | Pelati et al. | |

FOREIGN PATENT DOCUMENTS

| | | |
|---|---|---|
| EP | 0 905 112 | 3/1999 |
| EP | 0 905 112 | 8/2002 |
| EP | 1 216 219 | 2/2004 |
| EP | 1 255 719 | 5/2004 |
| RU | 455932 | 1/1975 |
| WO | WO 98/09929 | 3/1998 |
| WO | WO 98 09929 | 3/1998 |
| WO | WO 02/096844 | 12/2002 |
| WO | WO 03/050065 | 6/2003 |
| WO | WO 2003/053567 | 7/2003 |
| WO | WO 03/083014 | 10/2003 |
| WO | WO 2004/029178 | 4/2004 |
| WO | WO 2001/85872 | 11/2004 |

OTHER PUBLICATIONS

Co-pending Appl. No. PCT/US05/003772, Filed Feb. 4, 2005, "Process for the Preparation of Dehydrogenated Hydrocarbon Compounds", Matthew T. Pretz et al.

INTEGRATED PROCESS FOR PRODUCING AN ALKENYL-SUBSTITUTED AROMATIC COMPOUND

This application claims the benefit of U.S. Provisional Application No. 60/179,690, filed Feb. 2, 2000.

This invention relates to a process of preparing an alkenyl-substituted aromatic compound, such as styrene, from an aromatic compound, such as benzene, and an alkane, such as ethane. Hydrogen is produced as a co-product of the process.

Alkenyl-substituted aromatic compounds, such as styrene and α-methylstyrene, are used in the production of thermoplastic polymers, such a polystryrenes, acrylonitrile-butadiene-styrene copolymers (ABS), styrene-acrylonitrile resins (SAN), styrene-butadiene elastomeric copolymers (SBR), and formulations for unsaturated polyester resins. Divinylbenzene (vinylstyrene) is also used as a polymerization monomer for special synthetic rubbers, ion-exchange resins, casting resins, and polyesters. Hydrogen has many uses, including as a fuel source and as a reactant in hydrogenation processes.

Styrene is conventionally prepared in a two-step process starting from benzene and ethylene. In the first step, benzene, obtained as a refinery product, is alkylated with ethylene to form ethylbenzene. In the second step, the ethylbenzene is dehydrogenated to form styrene. Ethylene for the alkylation step is typically derived from the thermal or steam cracking of saturated hydrocarbons rich in natural gas, ethane, propane, and butanes, or from the cracking of naphtha. The alkylation can be carried out in a vapor phase in the presence of Lewis acids or zeolites having a high silica/alumina molar ratio, such as zeolite ZSM-5. Alternatively, the alkylation can be conducted in a liquid phase in the presence of a variety of acidic zeolites, such as, zeolites beta and mordenite. More recent technology has been developed for the production of ethylbenzene from a dilute ethylene stream in a mixed phase reactor, as disclosed by ABB Lummus Global and CDTech in U.S. Pat. No. 5,756,872. Typically, the dilute ethylene stream is obtained from the offgases of a petroleum refinery fluid catalytic cracker operation (FCC). The dehydrogenation of ethylbenzene to styrene is typically conducted adiabatically or isothermally in the presence of a catalyst comprising a metal oxide or a mixture thereof, for example, iron oxide or chromium oxide, in combination with alkali oxides. Steam at about 800° C. is used as a source of energy and is directly premixed with the ethylbenzene.

The conventional method of preparing styrene possesses disadvantages in several regards. Firstly, the crackers used to prepare ethylene are highly costly to construct and maintain, and their operation is energy intensive. Secondly, the styrene production facility must be located at the site of the cracker, because the transportation of ethylene is too expensive. Thirdly, the ethylene needed for the alkylation step is required to be essentially pure, otherwise undesirable alkylated products are produced in the alkylation reactor and the lifetime of the alkylation catalyst is significantly reduced. Since ethane cracking produces a variety of products in addition to ethylene including, for example, propylene, acetylene, $C_4$ saturated and unsaturated hydrocarbons, and $C_5$ and $C_{9+}$ hydrocarbons, the effluent from the cracker must be separated, for example, by extractive distillation, fractionation, and/or selective hydrogenation, to obtain the pure ethylene. These separations significantly increase the cost of producing pure ethylene.

The more recent technology of using a dilute ethylene stream derived from offgases from FCC operations possesses similar disadvantages to those mentioned hereinabove. The styrene production facility must be located at the site of the petroleum refinery, and extensive separation and clean-up of the FCC effluent must be conducted to remove, for example, acid gases, trace contaminants that can affect alkylation catalyst lifetime, and $C_3$ and heavier hydrocarbons, so as to obtain an ethylene suitable for feeding into an alkylation unit. The obtention of a suitable ethylene stream accounts for about 40 percent of the raw material cost of ethylbenzene.

As an alternative to cracking processes, ethylene can be obtained from the dehydrogenation of ethane, as disclosed in U.S. Pat. No. 5,430,21 1 and EP-B 1-0,637,578. These processes rely on selective catalysts, such as platinum and/or gallium, and possibly one or more alkaline or alkaline-earth metal oxides on a support, such as mordenite zeolite or selected phases of alumina, to produce essentially clean and dilute streams of ethylene in ethane. Dilute ethylene streams produced from these dehydrogenation processes are known to successfully alkylate benzene to ethylbenzene, as disclosed, for example, in U.S. Pat. No. 5,430,211 of The Dow Chemical Company.

Most recently, a process for producing styrene has been disclosed in EP-A2-0,905,112, which combines the dehydrogenation of ethane and ethylbenzene in one reactor to yield concurrently ethylene and styrene. Integrated into the overall process is an alkylation stage for producing the ethylbenzene from benzene and a recycle ethylene stream derived from the dehydrogenation reactor. The process involves (a) feeding to an alkylating unit a stream of benzene and a stream of recycled product containing ethylene; (b) mixing the stream at the outlet of the alkylation unit, containing ethylbenzene, with a stream containing ethane; (c) feeding the mixture thus obtained to a dehydrogenation unit containing a catalyst capable of concurrently dehydrogenating ethane to ethylene and ethylbenzene to styrene; (d) feeding the product leaving the dehydrogenation unit to a separation unit to produce a stream essentially containing styrene and a stream containing ethylene; and (e) recycling the stream containing ethylene to the alkylation unit. In another aspect of this process, a stream containing hydrogen, ethylene, and ethane derived from the dehydrogenation effluent is separated by way of a membrane filter to remove hydrogen, and the enriched ethylene and ethane stream is recycled to the alkylation reactor.

The aforementioned integrated process advantageously eliminates the need for an ethylene cracker. On the downside, however, the recovery of aromatics in this process is inefficient. Accordingly, unrecovered aromatics, including unrecovered ethylbenzene, are recycled to the alkylation reactor where they are alkylated to form a disadvantageously high level of heavies and tars. As a further disadvantage of this process, the separation of hydrogen from the recycle stream containing ethane and ethylene is inefficient. Accordingly, the recycle stream contains a concentration of hydrogen which disadvantageously lowers conversions of ethane and ethylbenzene in the dehydrogenation reactor. Moreover, a disadvantageous loss of ethane into the hydrogen stream occurs. No energy is recovered from the separation.

In view of the above, improvements in the process for producing alkenyl-substituted aromatic compounds are needed. More specifically, it would be advantageous to have a process that does not require an olefin cracker, such as an ethylene or propylene cracker, and that does not require the separation and purification of cracking effluents to prepare an olefin suitable for direct feeding into an alkylation unit. In this aspect alone, the cost of producing the alkenyl-substituted aromatic compound would be significantly reduced. It would also be advantageous to have a process that has a high efficiency aromatics recovery unit, such that no significant concentration of aromatics other than the raw material aromatic, such as benzene in the case of preparing styrene, is recycled to the alkylation reactor and no significant concentration of aromatics other than the desired alkylated aromatic, such as ethylbenzene in the case of preparing styrene, is recycled to the dehydrogenation reactor. Such a process would yield fewer undesirable by-products and longer catalyst lifetimes. It would also be advantageous to have a process wherein the hydrogen produced during dehydrogenation is efficiently separated from any recycle stream to the dehydrogenation reactor, so that there is no reduction in conversions in the dehydrogenation step. Since hydrogen is a valuable commodity, it would be a further advantage to recover the hydrogen produced in the dehydrogenation process.

This invention is a novel integrated process of preparing an alkenyl-substituted aromatic compound by using a $C_{6-12}$ aromatic compound and a $C_{2-5}$ alkane as raw materials. Hydrogen is produced as a co-product in this novel process. The process of this invention comprises:

(a) contacting a $C_{2-5}$ alkane and a $C_{2-5}$ alkyl-substituted aromatic compound in a dehydrogenation reactor in the presence of a dehydrogenation catalyst under process conditions sufficient to prepare a dehydrogenation effluent stream comprising a $C_{2-5}$ alkenyl-substituted aromatic compound, a $C_{2-5}$ alkyl-substituted aromatic compound, a $C_{2-5}$ alkane, a $C_{2-5}$ alkene, and hydrogen;

(b) separating the dehydrogenation effluent stream under conditions sufficient to obtain an essentially non-aromatic, gaseous stream comprising the $C_{2-5}$ alkane, the $C_{2-5}$ alkene, and hydrogen and an aromatics stream comprising the $C_{2-5}$ alkenyl-substituted aromatic compound and the $C_{2-5}$ alkyl-substituted aromatic compound, the total aromatics recovery being greater than about 90 weight percent;

(c) feeding the essentially non-aromatic, gaseous stream comprising the $C_{2-5}$ alkane, the $C_{2-5}$ alkene, and hydrogen into an alkylation reactor wherein the stream is contacted with a $C_{6-12}$ aromatic compound in the presence of an alkylation catalyst under process conditions sufficient to prepare an alkylation effluent stream comprising a $C_{2-5}$ alkyl-substituted aromatic compound, and optionally, poly($C_{2-5}$ alkyl-substituted) aromatic compound(s), and optionally, unreacted $C_{6-12}$ aromatic compound, and a gaseous stream comprising hydrogen and the $C_{2-5}$ alkane;

(d) separating the alkylation effluent stream under conditions sufficient to recover a $C_{2-5}$ alkyl-substituted aromatic compound fraction, and optionally, a poly($C_{2-5}$ alkyl-substituted) aromatic compound(s) fraction, and optionally, a $C_{6-12}$ aromatic compound fraction;

(e) recycling the $C_{2-5}$ alkyl-substituted aromatic compound recovered from steps (b) and (d) into the dehydrogenation reactor of step (a);

(f) separating the gaseous stream comprising the $C_{2-5}$ alkane and hydrogen, obtained from the alkylation reactor of step (c), under conditions sufficient to obtain an essentially pure stream of hydrogen and an essentially pure stream of $C_{2-5}$ alkane; and (g) recycling the $C_{2-5}$ alkane from step (f) into the dehydrogenation reactor of step (a).

The process of this invention provides a novel integrated method of preparing a $C_{2-5}$ alkenyl-substituted aromatic compound, such as styrene, from a $C_{6-12}$ aromatic compound, such as benzene, and a $C_{2-5}$ alkane, such as ethane. The novel process integrates three processes: (1) the dehydrogenation of a $C_{2-5}$ alkane to form a stream of $C_{2-5}$ alkene in $C_{2-5}$ alkane; (2) the alkylation of a $C_{6-12}$ aromatic compound with the stream comprising the $C_{2-5}$ alkene in the $C_{2-5}$ alkane to form the corresponding $C_{2-5}$ alkyl-substituted aromatic compound; and (3) the dehydrogenation of the $C_{2-5}$ alkyl-substituted aromatic compound to a $C_{2-5}$ alkenyl-substituted aromatic compound. As one advantage of the process of this invention, the dehydrogenations of the $C_{2-5}$ alkane and the $C_{2-5}$ alkyl-substituted aromatic compound are run concurrently in the same reactor using a catalyst which is capable of the dual dehydrogenations. As a significant advantage, the process of this invention does not require a cracker to produce the $C_{2-5}$ alkene. Accordingly, the process of this invention eliminates the high costs of constructing and maintaining a cracker facility and the high costs of the separations and purifications units associated with retrieving pure $C_{2-5}$ olefin from cracker effluents. Since the process of this invention relies on $C_{2-5}$ alkanes as a raw material and since such alkanes are readily available, the process of this invention can be advantageously located at any desired site independent of a petroleum refinery and olefin cracker facility. Ethane and propane, for example, are widely available at reasonable cost, whereas ethylene and propylene are not. As an even further advantage, the process of this invention possesses a high efficiency aromatics recovery stage, which results in higher selectivities to $C_{2-5}$ alkyl-substituted aromatics and $C_{2-5}$ alkenyl-substituted aromatics, lower selectivities to undesirable by-products, such as heavies and tars, and longer lifetimes for the alkylation and dehydrogenation catalysts. Most advantageously, the process of this invention efficiently separates hydrogen from $C_{2-5}$ alkane, so that high conversions of $C_{2-5}$ alkane and $C_{2-5}$ alkyl-substituted aromatic compound are achieved in the dehydrogenation step. The recovered hydrogen beneficially satisfies commercial grade purity standards, being about 99 percent pure. As an additional advantage of this invention, the hydrogen recovery utilizing a turboexpander produces energy for operation of the dehydrogenation and alkylation stages or for other unit operations or downstream processes.

The novel process of this invention is an integrated process of preparing a $C_{2-5}$ alkenyl-substituted aromatic compound using a $C_{2-5}$ alkane and a $C_{6-12}$ aromatic compound as raw starting materials. Essentially pure, chemical grade hydrogen is produced as a co-product of this process, and energy is recovered from the procesess for use in the unit process operations or other downstream operations. The unique process of this invention comprises:

(a) contacting a $C_{2-5}$ alkane and a $C_{2-5}$ alkyl-substituted aromatic compound in a dehydrogenation reactor in the presence of a dehydrogenation catalyst under process conditions sufficient to prepare a dehydrogenation effluent stream comprising a $C_{2-5}$ alkenyl-substituted aromatic compound, a $C_{2-5}$ alkyl-substituted aromatic compound, a $C_{2-5}$ alkane, a $C_{2-5}$ alkene, and hydrogen;

(b) separating the dehydrogenation effluent stream under conditions sufficient to obtain an essentially non-aromatic, gaseous stream comprising the $C_{2-5}$ alkane, the $C_{2-5}$ alkene, and hydrogen and an aromatics stream comprising the $C_{2-5}$ alkenyl-substituted aromatic compound and the $C_{2-5}$ alkyl-substituted aromatic compound, the total aromatics recovery being greater than about 90 weight percent;

(c) feeding the essentially non-aromatic, gaseous stream comprising the $C_{2-5}$ alkane, the $C_{2-5}$ alkene, and hydrogen into an alkylation reactor wherein the stream is contacted with a $C_{6-12}$ aromatic compound in the presence of an alkylation catalyst under process conditions sufficient to prepare an alkylation effluent stream comprising the $C_{2-5}$ alkyl-substituted aromatic compound, and optionally, poly($C_{2-5}$ alkyl-substituted) aromatic compound(s), and optionally, unreacted $C_{6-12}$ aromatic compound, and a gaseous stream comprising hydrogen and the $C_{2-5}$ alkane;

(d) separating the alkylation effluent stream under conditions sufficient to recover a $C_{2-5}$ alkyl-substituted aromatic compound fraction, and optionally, a poly($C_{2-5}$ alkyl-substituted) aromatic compound(s) fraction, and optionally, a $C_{6-12}$ aromatic compound fraction;

(e) recycling the $C_{2-5}$ alkyl-substituted aromatic compound recovered from steps (b) and (d) into the dehydrogenation reactor of step (a);

(f) separating the gaseous stream comprising the $C_{2-5}$ alkane and hydrogen, obtained from the alkylation reactor of step (c), under conditions sufficient to obtain an essentially pure stream of hydrogen and an essentially pure stream of $C_{2-5}$ alkane; and (g) recycling the $C_{2-5}$ alkane from step (f) into the dehydrogenation reactor of step (a).

In another aspect of this invention, optionally, the poly($C_{2-5}$ alkyl-substituted) aromatic compound(s) recovered from the alkylation effluent stream can be fed to a transalkylator where they can be transalkylated with the $C_{6-12}$ aromatic compound in the presence of a transalkylation catalyst under conditions sufficient to prepare additional $C_{2-5}$ alkyl-substituted aromatic compound. Thereafter, the $C_{2-5}$ alkyl-substituted aromatic compound obtained from the transalkylator can be recycled to the dehydrogenation reactor for dehydrogenation to $C_{2-5}$ alkenyl-substituted aromatic compound.

In yet another aspect of this invention, the hydrogen recovered from the process can be fed through a turboexpander to recover energy for use in operation of the dehydrogenation and alkylation stages, or for use in other unit operations or downstream operations. The hydrogen product recovered from the overall process meets commercial grade specifications for purity.

In a preferred aspect of this invention, the $C_{2-5}$ alkane is selected from the group consisting of ethane, propane, and butanes. In another preferred aspect of this invention, the $C_{6-12}$ aromatic compound is benzene. In yet another preferred aspect of this invention, the $C_{2-5}$ alkenyl-substituted aromatic compound is selected from styrene, □-methylstyrene, vinyltoluene, and divinylbenzene.

In a highly preferred embodiment of this invention, the $C_{2-5}$ alkane is ethane, the $C_{6-12}$ aromatic compound is benzene, and the $C_{2-5}$ alkenyl-substituted aromatic compound is styrene. In this preferred aspect the process comprises:

(a) contacting ethane and ethylbenzene in a dehydrogenation reactor in the presence of a dehydrogenation catalyst under process conditions sufficient to prepare a dehydrogenation effluent stream comprising styrene, ethylbenzene, ethane, ethylene, and hydrogen;

(b) separating the dehydrogenation effluent stream under conditions sufficient to obtain an essentially non-aromatic, gaseous stream comprising ethane, ethylene, and hydrogen, and an aromatics stream comprising styrene and ethylbenzene, the total aromatics recovery being greater than about 90 weight percent;

(c) feeding the essentially non-aromatic, gaseous stream comprising ethane, ethylene, and hydrogen into an alkylation reactor wherein the stream is contacted with benzene in the presence of an alkylation catalyst under process conditions sufficient to prepare an alkylation effluent stream comprising ethylbenzene, optionally, polyethylbenzene(s), and optionally, benzene, and a gaseous stream comprising hydrogen and ethane;

(d) separating the alkylation effluent stream under conditions sufficient to recover an ethylbenzene fraction, optionally, a polyethylbenzene(s) fraction, and optionally, a benzene fraction;

(e) recycling the ethylbenzene fraction recovered from steps (b) and (d) into the dehydrogenation reactor of step (a);

(f) separating the gaseous stream comprising ethane and hydrogen, obtained from the alkylation reactor of step (c), under conditions sufficient to obtain an essentially pure stream of hydrogen and an essentially pure stream of ethane; and

(g) recycling the ethane from step (f) into the dehydrogenation reactor of step (a).

Figure 1:
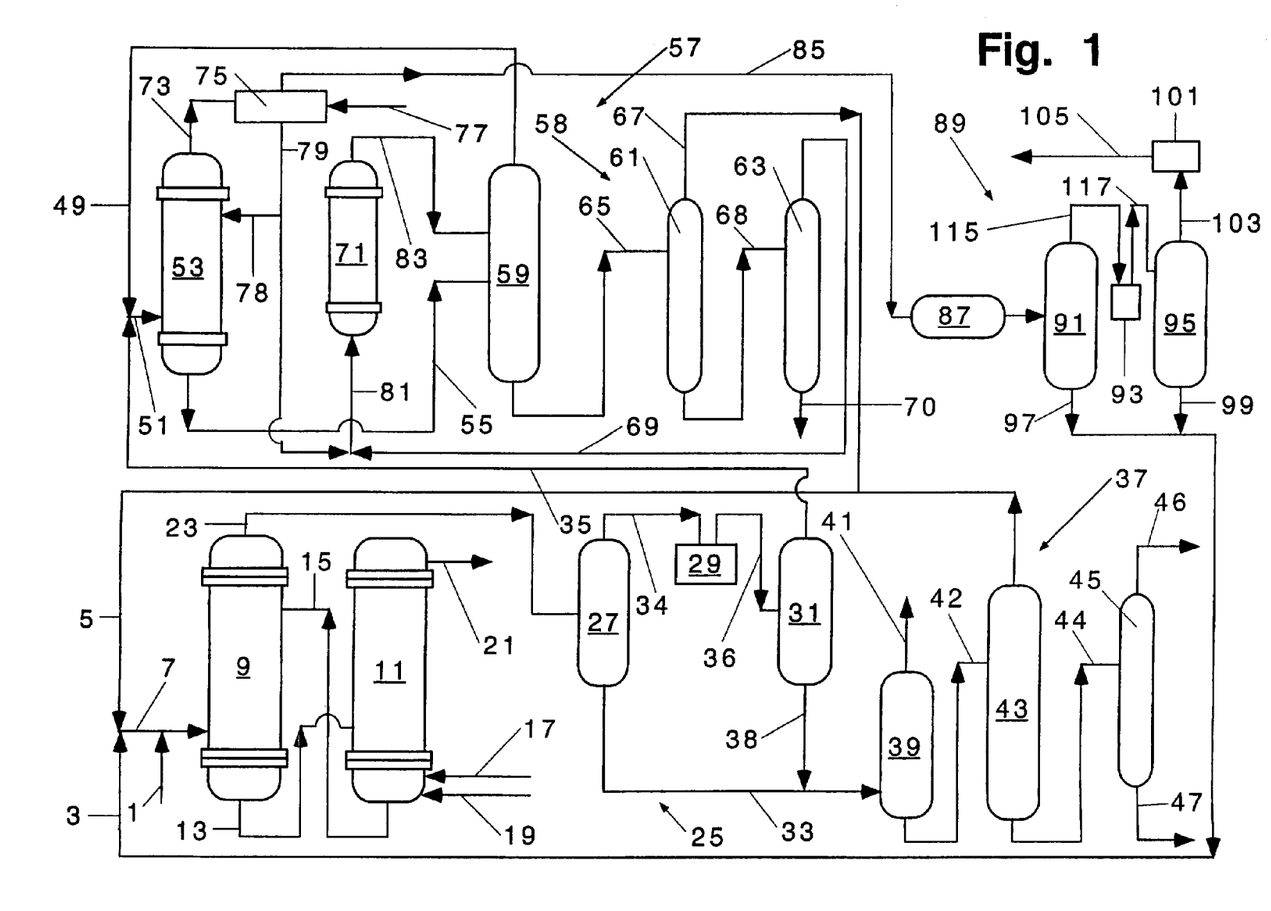
FIG. 1 illustrates in a schematic flowsheet the process of this invention as drawn towards the production of ethylbenzene using benzene and ethane as raw materials. A detailed description of FIG. 1 is set forth hereinafter.

The more preferred process described hereinabove for the production of styrene from benzene and ethane is illustrated in FIG. 1. With reference to FIG. 1, ethane is fed from ethane feed line 1 with recycle ethane from recycle ethane feed line 3 and ethylbenzene from ethylbenzene feed line 5 feeds by combining these streams in dehydrogenation reactor feed line 7, which is fed to the dehydrogenation reactor 9. The dehydrogenation catalyst (not shown) in the dehydrogenation reactor 9 is circulated to a catalyst regenerator 11 via exit line 13, where the catalyst, which is at least partially deactivated, is regenerated and then returned to the dehydrogenation reactor 9 via catalyst feed line 15. Catalyst regeneration takes place by heating the catalyst with fuel and air admitted to the catalyst regenerator 11 via fuel line 17 and air line 19 with the flue gas exiting the catalyst regenerator 11 via flue gas line 21. The dehydrogenation effluent stream exits from the dehydrogenation reactor 9 via dehydrogenation effluent line 23 and is fed to a first separations unit 25 comprising, for example, a first separator 27, a compressor 29, and a second separator 31 to yield an aromatics effluent stream, which exits from the bottom of first separator 27 via aromatics effluent line 33, and a reduced aromatics stream overhead from first separator 27 via reduced aromatics line 34, which is fed to the low pressure side of compressor 29. A higher pressure stream of reduced aromatics exits compressor 29 via high pressure line 36 to the second separator 31 from which an essentially non-aromatics overhead gas stream is taken via essentially non-aromatics overhead gas line 35. The separator/compressor sequence may be repeated one or more times to achieve the desired degree of aromatics recovery via recycle lines (not shown) or, alternatively, via the addition of one or more similar separators and compressors. The recovered aromatics in aromatics effluent line 33 and in the bottoms stream from the second separator 31 via second separator bottoms line 38, containing unreacted benzene, ethylbenzene, and styrene, are separated in a three-column distillation train 37 to yield a fraction containing benzene from benzene column 39 via benzene line 41, ethylbenzene from ethylbenzene column 43, and styrene via styrene product line 46 from styrene column 45. The bottoms stream from benzene column 39 is taken via benzene column bottoms line 42 to feed the ethylbenzene column 43. The ethylbenzene column bottoms stream is taken by ethylbenzene column bottoms line 44 to feed the styrene column 45. The styrene bottoms is a tar which is sent to fuel or waste disposal (not shown) via tar line 47. The ethylbenzene fraction is recycled into ethylbenzene feed line 5 and then to the dehydrogenation reactor 9 via dehydrogenation reactor feed line 7. The resultant essentially non-aromatic stream in essentially non-aromatic overhead gas line 35, containing unreacted ethane, ethylene, and hydrogen from the second separator 31, is fed via essentially non-aromatic overhead gas line 35, combined with benzene from benzene recycle line 49 into alkylation reactor feed line 51, and is then fed into the alkylation reactor 53. The bottoms from the alkylation reactor 53 are fed via alkylation bottoms line 55 into a separation unit 57, for example, a three column distillation train 58 wherein an essentially pure fraction of benzene is obtained as overheads from second benzene column 59, an essentially pure fraction of ethylbenzene is obtained as overheads from second ethylbenzene column 61, polyethylbenzenes are obtained as overheads from polyethylbenzene column 63, and a residual stream of tars are obtained as bottoms from polyethylbenzene column 63. The benzene fraction is recycled into benzene recycle line 49 and fed to the alkylation reactor 53. The bottoms stream from second benzene column 59 is fed to the second ethylbenzene column 61 via second benzene column bottoms line 65. The ethylbenzene fraction taken overhead from second ethylbenzene column 61 via second ethylbenzene column overhead line 67 and is recycled into ethylbenzene feed line 5 and fed into the dehydrogenation reactor 9. The bottoms stream from the second ethylbenzene column 61 is fed via second ethylbenzene column bottoms line 68 into polyethylbenzene column 63 from which an overhead polyethylbenzene fraction is obtained, via polyethylbenzene column overhead line 69, and a bottoms (tar) fraction is obtained via polyethylbenzene column bottoms line 70. The polyethylbenzene fraction can be recycled via polyethylbenzene line 69 and transalkylator feed line 81 into a transalkylation reactor 71 and reacted with benzene, obtained for example from the separation of the alkylation reactor 53 effluent taken overhead via line 73 and separated in a gas separator 75 also fed with fresh benzene via fresh benzene feed line 77, from which gas separator 75 is obtained overhead gaseous hydrogen and ethane stream 85 and liquid benzene bottoms stream 79. Liquid benzene is fed via gas separator liquids line 79 with polyethylbenzene into transalkylation reactor 71 via transalkylator reactor feed line 81 to form additional ethylbenzene, which is also fed via transalkylator overhead line 83 and separated in the three column distillation train 58 noted hereinbefore. The recovered ethylbenzene is ultimately fed to the dehydrogenation reactor 9. The overhead gaseous product stream from the alkylation reactor 53 may be stripped to remove any aromatics in the gas separator 75, and the resulting gas stream containing ethane and hydrogen is sent via gas separator overhead gaseous product line 85 to a cryo-cooler 87 and second separator unit 89 comprising, for example, separator 91, a turboexpander 93 and an additional separator 95. An essentially pure ethane stream, obtained from the separators, is taken via bottoms lines 97 and additional separator bottoms line 99, respectively, and recycled via recycle ethane feed line 3 into the dehydrogenation reactor 9. An essentially pure hydrogen stream, which may optionally be compressed in compressor 101, is obtained overhead from additional separator overhead line 103 and hydrogen product line 105 for sale or for use in the process or in another unit at the site.

Figure 2:
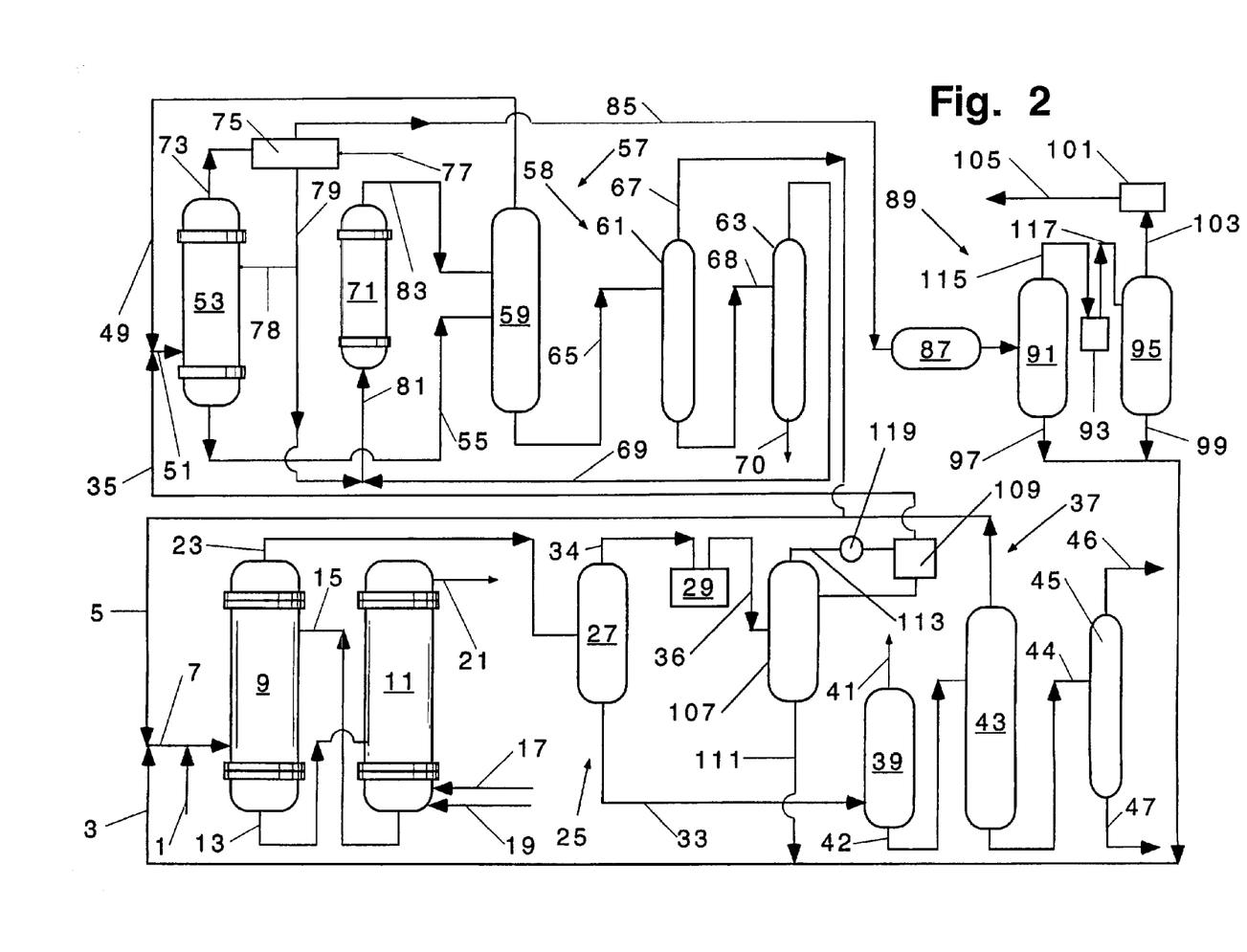
FIG. 2 illustrates in a schematic flowsheet the process of this invention as shown in FIG. 1, with the exception that separator 31 is replaced with a splitter tower 107, overhead condenser 119, and reflux drum 109, the unit designed to enrich the alkene concentration of the feed to the alkylation reactor. A detailed description of FIG. 2 is also set forth hereinafter.

A variation of the aforementioned process is seen in FIG. 2, wherein the unit operations are identical to those in FIG. 1, with the exception that an alkane/alkene splitter unit, such as distillation tower 107 and overhead refrigeration condenser 119, and optional drip or reflux drum 109, is added after separator 27/compressor 29 units. The alkane/alkene splitter unit is designed to enrich the gaseous feed to the alkylation reactor 53 in alkene, which in this illustration is ethylene.

The aromatic compound which is fed to the alkylation reactor 53 in the process of this invention is any $C_{6-12}$ aromatic compound which is capable of being alkylated to an alkyl-substituted $C_{6-12}$ aromatic compound. Preferably, the $C_{6-12}$ aromatic compound is an unsubstituted or substituted benzene. More preferably, the $C_{6-12}$ aromatic compound is represented by the following formula:

wherein n is an integer from 0 to about 3, and each $R^1$ is independently selected from the group consisting of hydrogen and $C_{1-5}$ alkyl moieties, more preferably, from methyl, ethyl, and propyl moieties, with the balance of the 6-n bonds being to hydrogen. Non-limiting examples of $C_{6-12}$ aromatic compounds which satisfy the aforementioned formula include benzene, toluene, xylenes, ethylbenzene, ethyltoluene, diethylbenzene, isopropylbenzene, and t-butylbenzene. Most preferably, the $C_{6-12}$ aromatic compound is benzene.

The alkane, which is fed to the dehydrogenation reactor, is any $C_{2-5}$ alkane which is capable of being dehydrogenated to the corresponding $C_{2-5}$ alkene. Suitable examples of $C_{2-5}$ alkanes include ethane, propane, n-butane, isobutane, and the various isomers of pentane. More preferably, the $C_{2-5}$ alkane is ethane or propane, and the corresponding $C_{2-5}$ alkene is ethylene or propylene.

The reaction of the $C_{2-5}$ alkene with the $C_{6-12}$ aromatic compound in the alkylation reactor results in a $C_{2-5}$ alkyl-substituted aromatic compound which preferably is represented by the formula:

wherein n is an integer from 0 to about 3; each $R^1$ is independently selected from the group consisting of hydrogen and $C_{1-5}$ alkyl moieties; and $R^2$ is selected from $C_{2-5}$ alkyl moieties, with the balance of the 5-n bonds being to hydrogen. More preferred $C_{2-5}$ alkyl-substituted aromatic compounds consistent with the aforementioned formula include ethylbenzene, ethyltoluene, isopropylbenzene, diethylbenzene, and di(isopropyl)benzene. During the dehydrogenation step, $R^2$ is transformed from a $C_{2-5}$ alkyl moiety into a $C_{2-5}$ alkenyl moiety. The more preferred $C_{2-5}$ alkenyl-substituted aromatic products include styrene, α-methylstyrene, vinyltoluene, and divinylbenzene.

Reference is made again to FIG. 1 wherein in a first stage, the $C_{2-5}$ alkyl-substituted aromatic compound and the $C_{2-5}$ alkane are fed as dehydrogenation reactor feed line 7 to the dehydrogenation reactor 9 where the reactants contact a dehydrogenation catalyst. The dehydrogenation reactor 9 can have any conventional design including, for example, fixed bed, fluidized bed, and transport bed designs, provided that the dehydrogenation proceeds concurrently to the desired $C_{2-5}$ alkene and $C_{2-5}$ alkenyl-substituted aromatic products. Any dehydrogenation catalyst can be employed in the dehydrogenation step, provided that the catalyst is capable of dehydrogenating the $C_{2-5}$ alkane to the corresponding $C_{2-5}$ alkene and concurrently dehydrogenating the $C_{2-5}$ alkyl-substituted aromatic compound to the corresponding $C_{2-5}$ alkenyl-substituted aromatic compound. Likewise, any process conditions, including for example temperature, pressure, space velocity, and molar ratio of $C_{2-5}$ alkyl-substituted aromatic compound to $C_{2-5}$ alkane (for example, molar ratio of ethylbenzene to ethane) can be employed, provided that the desired $C_{2-5}$ alkenyl-substituted aromatic compound and $C_{2-5}$ alkene are produced.

A preferred dehydrogenation reactor, preferred dehydrogenation catalysts, and preferred process conditions are described in EP-A2-0,905,112, EP-B1-0,637,578, and U.S. Pat. No. 5,430,211. As described in these references, the dehydrogenation reaction is carried out in gaseous phase operating in a fixed bed or fluidized bed catalytic reactor, with fluidized bed reactors being preferred for their technological advantages, which are known to those skilled in the field. One preferred catalyst for the dehydrogenation reaction is based on gallium and platinum supported on alumina in the delta or theta phase, or in a mixture of delta plus theta phases, or theta plus alpha phases, or delta plus theta plus alpha phases, modified with silica, and having a surface area preferably less than about 100 m²/g, as determined by the BET method known to those skilled in the field. More preferably, the catalyst comprises:

i) from 0.1 to 34 percent, most preferably, from 0.2 to 3.8 percent, by weight of gallium oxide ($Ga_2O_3$);

ii) from 1 to 99 parts per million (ppm), most preferably, from 3 to 80 ppm, by weight of platinum;

iii) from 0.05 to 5 percent, most preferably, from 0.1 to 3 percent, by weight of an alkaline and/or alkaline-earth oxide, for example potassium oxide;

iv) from 0.08 to 3 percent by weight silica;

v) the balance to 100 percent being alumina.

Another preferred catalyst for the dehydrogenation reaction is based on chromium and comprises:

i) from 6 to 30 percent, preferably, from 13 to 25 percent, by weight of chromium oxide ($Cr_2O_3$);

ii) from 0.1 to 3.5 percent, most preferably, from 0.2 to 2.8 percent, by weight stannous oxide (SnO);

iii) from 0.4 to 3 percent, most preferably, from 0.5 to 2.5 percent, by weight of an alkaline oxide, for example, potassium oxide;

iv) from 0.08 to 3 percent by weight silica;

v) the balance to 100 percent being alumina in the delta or theta phase, or a mixture of delta plus theta phases, or theta plus alpha phases, or delta plus theta plus alpha phases.

The catalysts mentioned hereinabove can be used as such or diluted with an inert material, for example, alpha-alumina, possibly modified with oxides of alkaline metals and/or silica, at a concentration of the inert product of between 0 and 50 percent by weight.

Details on the preparation of the aforementioned catalysts and their more preferred species can be found in EP-A2-0, 905,112 and EP-B1-0,637,578. Typically, the process of preparing the aforementioned dehydrogenation catalysts comprises dispersing precursors of the catalytic metals, for example, solutions of soluble salts of the catalytic metals, onto the carrier consisting of alumina or silica. An example of dispersion can comprise impregnation of the carrier with one or more solutions containing the precursors of gallium and platinum, or with one or more solutions of the precursors of chromium and tin, followed by drying and calcination. An alternative method comprises ion adsorption, followed by the separation of the liquid portion of the adsorption solution, drying, and activation of the resultant solid. As another alternative, the carrier can be treated with volatile species of the desired metals. In the case of added alkaline or alkaline earth metals, the addition procedure comprises co-impregnation of the alkaline or alkaline earth metal with the primary catalytic metals (that is, Ga and Pt, or Cr and Sn), or alternatively, addition of the alkali or alkaline earth metal to the carrier prior to dispersion of the primary catalytic metals, and thereafter, possible calcination of the solid.

Other suitable dehydrogenation catalysts, based on iron oxide, are disclosed in Japanese Kokai JP 7-328439 and more preferably disclosed in International Patent Application No. PCT/EP00/09196, filed by Snamprogetti on Sep. 19, 2000, naming Rodolfo Iezzi and Domenico Sanfilippo as inventors. In the description of patent application No. PCT/EP00/09196, the iron oxide catalyst comprises:

(i) from 1 to 60 percent, preferably from 1 to 20 percent, by weight iron oxide;

(ii) from 0.1 to 20 percent, preferably from 0.5 to 10 percent, by weight of at least one alkaline or alkaline earth metal oxide, more preferably, potassium oxide;

(iii) from 0 to 15 percent, preferably, from 0.1 to 7 percent, by weight of at least one rare earth oxide, preferably, selected from the group consisting of cerium oxide, lanthanum oxide, praseodymium oxide, and mixtures thereof;

(iv) the complement to 100 percent being a carrier consisting of a microspheroidal alumina with a diameter selected from those in delta or theta phase, or in a mixture of theta plus alpha phases, or in a mixture of delta plus theta plus alpha phases, modified preferably with from 0.08 to 5.0 weight percent of silica.

The carrier in the preferred iron oxide catalyst more preferably has an average particle diameter and particle density such that the final product can be classified as Group-A according to Geldart (*Gas Fluidization Technology*, D. Geldart, John Wiley & Sons) and a surface area of less than about 150 m²/g, as measured by the BET method known to those skilled in the art.

The process of preparing the iron oxide catalyst described hereinabove can be generally carried out by means of the following steps: (1) preparation of solutions based on derivatives of the components of the catalyst; (2) dispersion of the solution(s) containing the alkaline or alkaline earth metal oxides and rare earth oxides onto the carrier, for example, by impregnation, ion-exchange, vapor deposition, or surface adsorption; (3) drying of the resulting solids at 100° C. to 150° C.; (4) optionally, calcination of the dried solids at a temperature less than about 900° C.; (5) dispersion of the solution containing the iron precursor and, optionally, additional solution(s) containing precursors of the alkaline or alkaline earth metal oxides and rare earth oxides; (6) drying of the resulting solids at 100° C. to 150° C., and (7) calcination of the dried solids at a temperature ranging from 500° C. to 900° C. To give a specific example, a microspheroidal pseudobohemite alumina, to which silica (about 1.2 percent by weight) has been added, may be prepared as a carrier having a particle diameter ranging from 5 to 300 microns, by spray drying a sol of hydrated alumina and Ludox™ brand silica. The sample may be calcined at about 450° C. for about 1 hour and then at about 1,190° C. for about 4 hours in a stream of dry air. The product obtained, consisting of delta, theta, and alpha transition alumina, has a surface area of about 34 $m^2/g$ and a porosity of about 0.22 cc/g. The thusly-prepared microspheroidal alumina may be impregnated, using the "incipient wetness" procedure known to those skilled in the art, with an aqueous solution containing potassium nitrate in deionized water, maintained at a temperature of about 25° C. The impregnated product may be dried at about 80° C. and then calcined in a stream of dry air at about 650° C. for about 4 hours. The alumina modified with potassium oxide may be impregnated with a second aqueous solution containing ferric nitrate and potassium nitrate, then dried at about 120° C. for about 4 hours. The impregnated product may be dried at about 120° C. for about 12 hours and finally calcined at about 700° C. for about 4 hours to yield the supported iron oxide catalyst. Based on the molarity of the solutions and the amount of solution deposited, the weight composition of the formulate could be suitably prepared to be about 6.6 percent $Fe_2O_3$, about 4 percent $K_2O$ and carrier complement to 100 percent.

Another preferred dehydrogenation catalyst consists essentially of a mordenite zeolite, optionally, promoted with a metal selected from gallium, zinc, the platinum group metals, or a combination thereof, as described in U.S. Pat. No. 5,430,211. The mordenite is preferably acid extracted and thereafter impregnated or ion-exchanged with one or more metals selected from gallium, zinc, and the platinum group metals, more preferably, gallium. In this catalyst, the total metal loading typically ranges from 0.1 to 20 weight percent, based on the total weight of the catalyst.

The dehydrogenation process conditions, including molar ratio of feedstock components, temperature, pressure, and gas hourly space velocity, can be varied depending upon the particular $C_{2-5}$ alkane and $C_{2-5}$ alkyl-substituted aromatic feedstock. To obtain a good balance between the dehydrogenation and alkylation processes, it is preferable to operate the dehydrogenation at a molar ratio of $C_{2-5}$ alkyl-substituted aromatic compound, for example ethylbenzene, to $C_{2-5}$ alkane, for example ethane, (calculated as total $C_{2-5}$ alkane from both a fresh feed and any recycle feed) in the range from 0.01/1 to 1/1. The dehydrogenation process is conducted at a temperature typically greater than about 450° C., and preferably, greater than about 530° C. The dehydrogenation process is carried out at a temperature typically less than about 700° C., and preferably, less than about 680° C. The pressure in the dehydrogenation reactor is typically greater than about 0.1 atmospheres (atm) absolute (1.47 psia, 10 kPa) preferably, greater than about 0.3 atm (4.4 psia, 30 kPa). The pressure is typically less than about 3.0 atm absolute (44.1 psia, 300 kPa), and preferably, less than about 1.5 atm (22.1 psia, 150 kPa). The flow rate of the reagents, expressed as the hourly volumetric flow-rate of the feed to the dehydrogenation reactor per liter of catalyst (Gas Hourly Space Velocity or GHSV), is typically greater than about 100 $h^{-1}$ and typically less than about 10,000 $h^{-1}$.

In the fluid-bed dehydrogenation reactor for the preferred dehydrogenation of ethane and ethylbenzene, it is preferable to operate at a temperature ranging from 450° C. to 650° C.; at a pressure of about atmospheric or slightly higher; and at a space velocity of between about 100$h^{-1}$ and about 1,000$h^{-1}$, more preferably, between about 150$h^{-1}$ and about 300$h^{-1}$, with a residence time of the catalyst in the fluid-bed zone typically varying from 5 to 15 minutes, preferably, from 10 to 15 minutes, and in a desorption zone wherein hydrocarbons are stripped from 0.2 to 10 minutes. Further details can be found in the art, for example, in EP-A2-0,905,112 and EP-B1-0,637,578.

During the dehydrogenation reaction, it is preferred to continuously remove the catalyst system (catalyst plus any inert material) from the reactor to a regenerator to be regenerated in the presence of a regeneration gas comprising oxygen and, optionally, a gaseous fuel, for example, methane, ethane, refinery fuel gas, and mixtures of these and/or other gaseous hydrocarbons. Any regeneration conditions which effectively regenerate the catalyst are acceptable. Generally, an excess of oxygen is employed above the stoichiometric ratio required for complete combustion of the gaseous fuel to carbon dioxide and water. Typically, from 5 to 15 mole percent excess, and preferably, about 10 mole percent excess, of oxygen is employed. It is also preferable to operate at a pressure which is atmospheric or slightly higher, at a regeneration gas hourly space velocity ranging from 100 $h^{-1}$ to 1,000 $h^{-1}$, and with a residence time of the catalyst particles varying from 5 to 60 minutes, and preferably, from 20 to 40 minutes. The regeneration temperature is generally between about 600° C. and about 700° C., and preferably, between about 620° C. and about 680° C. Additional details regarding the transportation of the catalyst to and from the regenerator and optional treatments of the catalyst, such as reduction, are further described in EP-A2-0,905,112.

The effluent stream from the dehydrogenation reactor, comprising $C_{2-5}$ alkenyl-substituted aromatic compound, $C_{2-5}$ alkene, hydrogen, and unconverted $C_{2-5}$ alkyl-substituted aromatic compound and $C_{2-5}$ alkane, is fed into a first separator wherein the stream is cooled to obtain a crude aromatics effluent stream comprising $C_{2-5}$ alkenyl-substituted aromatic compound and unconverted $C_{2-5}$ alkyl-substituted aromatic compound and a gas stream comprising $C_{2-5}$ alkane, $C_{2-5}$ alkene, hydrogen, and residual aromatics. The cooling temperature and pressure can be adjusted by one skilled in the art, depending upon the specific aromatic and non-aromatic components involved. With respect to a feed of styrene, ethylbenzene, ethane, and ethylene, the temperature is typically lowered to less than about 50° C., and preferably, to less than about 48° C., by any suitable cooling means or method, for example, a cross-feed exchanger. Typically for this specific feed, the temperature is maintained at greater than about 30° C., and preferably, greater than about 38° C. The pressure in the separator is maintained typically at greater than about 0.5 psig (3.5 kPa), and preferably, greater than about 1 psig (6.9 kPa). Typically, the pressure is maintained at less than about 50 psig (350 kPa), more preferably, less than about 10 psig (70 kPa). The separation is designed to result in an aromatics stream comprising predominantly $C_{2-5}$ alkenyl-substituted aromatic compound and unconverted $C_{2-5}$ alkyl-substituted aromatic compound, for example, predominantly styrene and unconverted ethylbenzene, and a vapor stream comprising hydrogen, $C_{2-5}$ alkene, such as ethylene, and $C_{2-5}$ alkane, such as ethane, as well as smaller amounts of other alkanes, such as methane, and uncondensed aromatics.

The vapor stream from the first separator is thereafter fed to a compressor where it is compressed, typically in a series of stages with intermediate condensation of aromatic products. Again, the compression pressure will depend upon the specific aromatic and non-aromatic components involved. In the case of a stream comprising ethylene, ethane, styrene, and ethylbenzene, compression is applied to a pressure typically greater than about 300 psig (2,069 kPa), and preferably, greater than about 350 psig (2,413 kPa). Typically, the pressure is less than about 600 psig (4,137 kPa), and preferably, less than about 550 psig (3,792 kPa). The compressed vapor stream is cooled to a temperature less than about 20° C., and preferably, less than about 10° C., but typically, greater than about 0° C., and preferably, greater than about 5° C. The cooled and compressed vapor stream is fed to a second separator wherein a second crude aromatics stream is recovered, also comprising predominantly $C_{2-5}$ alkenyl-substituted aromatic compound, for example styrene, and unconverted $C_{2-5}$ alkyl-substituted aromatic compound, for example, ethylbenzene. The compression and separation operations can be reiterated one or more times, until the desired yield of aromatics is achieved.

The aromatics recovered from the secondary and any subsequent separator(s) are combined with the first aromatics stream obtained from the first separator, and the combined "crude" aromatics stream is sent to a separation/purification unit for recovering an essentially pure fraction of $C_{2-5}$ alkenyl-substituted product, such as styrene, and an essentially pure fraction of unreacted $C_{2-5}$ alkyl-substituted aromatic compound, such as ethylbenzene. Any conventional separation/purification methods known to those skilled in the art can be employed, including fractional distillation, crystallization, and so forth. With respect to producing styrene, a distillation train is preferably employed wherein benzene and toluene are recovered in a first or benzene column; ethylbenzene is recovered in a second or ethylbenzene column; and essentially pure styrene is recovered in a third or styrene column. The recovered benzene can be recycled to the alkylation reactor, described hereinafter. The recovered $C_{2-5}$ alkyl-substituted aromatic, for example, ethylbenzene, can be recycled to the dehydrogenation reactor. The recovered styrene product is sent for further processing or storage. The overall aromatics recovery for the process of this invention is typically greater than about 90 weight percent, preferably, greater than about 95 weight percent, and more preferably, greater than about 99 weight percent, based on the total weight of initial aromatic feed to the alkylation reactor.

Typically, the vapor stream emanating at high pressure from the last separation unit contains greater than about 1 mole percent alkene, preferably, greater than about 3 mole percent alkene. Typically, the high pressure vapor stream contains less than about 40 mole percent alkene, preferably, less than about 20 mole percent alkene. Accordingly, the high pressure vapor stream may be referred to as a "dilute alkene stream" or, likewise, a "dilute olefin stream." Typically, the dilute alkene stream contains greater than about 5 mole percent hydrogen, preferably, greater than about 10 mole percent hydrogen. Typically, the dilute alkene stream contains less than about 60 mole percent hydrogen, preferably, less than about 40 mole percent hydrogen. Typically, the dilute alkene stream contains greater than about 0.01 mole percent methane, preferably, greater than about 0.05 mole percent methane. Typically, the dilute alkene stream contains less than about 5 mole percent methane, preferably, less than about 1 mole percent methane. The methane is formed primarily in the dehydrogenation reactor, but may also be present in small concentrations (parts per million) in the alkane feed. The balance of the stream comprises $C_{2-5}$ alkane. Typically, the $C_{2-5}$ alkane concentration is greater than about 20 mole percent, preferably, greater than about 40 mole percent. Typically, the $C_{2-5}$ alkane concentration is less than about 95 mole percent, preferably, less than about 85 mole percent.

FIG. 2 is identical to FIG. 1 in all respects, except as regards the treatment of the dilute stream of alkene in alkane obtained from the separation of the dehydrogenation effluent. Referring to FIG. 2, the dehydrogenation effluent in dehydrogenation effluent line 23 can be separated, as noted hereinabove, via cooling-compression in separation unit 25 (and reiterations thereof) to obtain a crude aromatics stream out of the bottom of first separator 27 via aromatics effluent line 33 and a gaseous stream comprising essentially $C_{2-5}$ alkene and hydrogen diluted in $C_{2-5}$ alkane in high pressure line 36. Thereafter, in this alternative embodiment, the dilute alkene stream in high pressure line 36 can be fed into a rough cut alkene-alkane splitter, comprising, for example, distillation tower 107 equipped with an overhead refrigeration condenser 119 and optional reflux or drip drum 109, via overhead line 113, to obtain an overhead stream in essentially non-aromatics overhead gas line 35 which is enriched in alkene. In this manner, the concentration of alkene can be increased to the alkylation reactor 53. The bottoms from the alkene-alkane splitter tower 107 comprise a gaseous stream enriched in alkane, which can be returned via alkene-alkane splitter tower bottoms line 111 to the dehydrogenation reactor via recycle ethane feed line 3.

The design of the alkene-alkane splitter unit (107, 119, 109) can be varied by one skilled in the art from a knowledge of the specific alkane and alkene to be split and the economics of different refrigeration methods. In theory, the splitting can be nearly complete with substantially pure streams of alkane and alkene obtained (>90 mole percent). In practice, the cost of obtaining substantially pure streams of alkane and alkene may be too high. Nevertheless, cost-effective splitting can be achieved to obtain enriched streams of alkane and alkene. For the splitting of ethane and ethylene, propylene refrigeration, which achieves a temperature of between −20° C. and −35° C., is cost effective; but refrigeration sources of lower temperatures may also be employed. With use of the splitter tower and propylene refrigeration, concentrations of greater than about 10 mole percent ethylene in the essentially non-aromatics gas stream, and preferably, greater than about 20 mole percent ethylene in the essentially non-aromatics gas stream, can be achieved. Under these conditions, typically the concentration of ethylene is less than about 70 mole percent in the essentially non-aromatics gas stream.

The olefin stream obtained from the last of the separators or the alkene-alkane splitter tower via essentially non-aromatics overhead gas line 35, now containing $C_{2-5}$ alkene, $C_{2-5}$ alkane, hydrogen, and optionally other alkanes, such as methane, is fed via essentially non-aromatics overhead gas line 35 to alkylation feed line 51 to the alkylation reactor 53. Recycle $C_{6-12}$ aromatic compound stream can also be fed via benzene recycle line 49 to alkylation feed line stream 51. Fresh $C_{6-12}$ aromatic compound, such as benzene, can be fed to the alkylation reactor, for example, via aromatic compound feed lines 77 to gas separator liquids line 79 and to alkylator feed line 78. In the production of styrene, for example, refinery grade benzene having a purity of more than about 95 percent by weight benzene is fed with the ethylene stream into the alkylation reactor 53. Any alkylation reactor can be employed in the process of this invention, including fixed bed, fluidized bed, transport bed, monolith reactors, and catalytic distillation reactors, provided that alkylation to the desired $C_{2-5}$ alkyl-substituted aromatic compound is achieved. Likewise, any alkylation catalyst can be used and any alkylation process conditions can be used, including for example, any molar ratio of $C_{6-12}$ aromatic compound to $C_{2-5}$ alkene, temperature, pressure, and space velocity, provided that the desired $C_{2-5}$ alkyl-substituted aromatic product is produced.

In one preferred mode of operation, the alkylation reactor 53 comprises a catalytic distillation reactor operating in a mixed liquid-gas phase mode, for example, as described in U.S. Pat. No. 5,476,978 and WO 98/09929. In a catalytic distillation reactor, the reactant and product components of the catalytic process, in this instance the alkylation process, are concurrently separated by distillation using the catalytic reactor and the catalyst itself as the distillation tower. Preferred alkylation catalysts include natural and synthetic porous crystalline solids suitable for mixed phase alkylation processes, such as, acidic zeolites with the general structure codes MWW, FAU, BEA, LTL, MAZ, LTA, MOR, ESV, OFF, and more specifically, zeolites Y, beta, mordenite, omega, A, X and L; as well as crystalline porous solids MCM-22, MCM-36, MCM49, MCM-56, and ERS-10. Preferably, the alkylation catalyst is selected from MCM-22 and zeolites beta, Y and mordenite, even more preferably, zeolite beta. Preferably, the silicon to aluminum atomic ratio of the zeolite ranges between 5/1 and 200/1.

In another preferred mode of operation, the alkylation reactor 53 comprises a continuous flow, fixed bed reactor operating in full gas phase, as described, for example, in U.S. Pat. No. 4,409,412 and U.S. Pat. No. 5,517,185. Suitable alkylation catalysts for the gas phase process include zeolites of the ZSM designation, such as, ZSM-5 (structure code MFI), ZSM-11, ZSM-12, ZSM-23, ZSM-35, ZSM-38, ZSM-48, and intergrowths thereof, as well as any of the aforementioned natural and synthetic porous crystalline solids mentioned hereinbefore, provided that the solid can tolerate the temperatures of the gas phase process and that the desired selectivity to alkyl-substituted aromatic compound is achieved. Preferably, the gas phase alkylation catalyst is a zeolite of the ZSM designation, more preferably, ZSM-5, even more preferably, ZSM-5 having a silicon to aluminum atomic ratio in the range from 20/1 to 200/1.

Optionally, any of the aforementioned alkylation catalysts may be bound with a binder, for the purpose, for example, of improving the catalyst's strength or attrition resistance. Suitable binders include, but are not limited to silicas, aluminas, silica-aluminas, aluminosilicates, and clays, such binders being known to those skilled in the art.

With respect to the preferred process of alkylating benzene with ethylene, the molar ratio of benzene to ethylene, which is suitably employed in the catalytic zone of the alkylation reactor, is typically greater than about 1.8/1, and preferably, greater than about 2.0/1. The molar ratio of benzene to ethylene in the reaction zone is typically less than about 100/1, and preferably, less than about 50/1, and more preferably, less than about 10/1. The temperature will vary depending upon the reactor design; but typically, the temperature is greater than about 50° C. and less than about 450° C. For gas phase processes, the temperature is preferably greater than about 325° C., more preferably, greater than about 350° C., but preferably, less than about 450° C. The temperature of the catalytic distillation reactor will vary along the bed. Preferably, the temperature in the catalytic distillation mixed phase reactor is greater than about 140° C., and more preferably, greater than about 200° C., but preferably less than about 350° C., and more preferably, less than about 300° C. The pressure in the alkylation reactor is typically greater than about 3 psig (21 kPa), preferably, greater than about 100 psig (690 kPa), and more preferably, greater than about 350 psig (2,413 kPa). The pressure is typically less than about 750 psig (5,171 kPa), preferably, less than about 650 psig (4,482 kPa), and more preferably, less than about 500 psig (3,447 kPa). The benzene weight hourly space velocity (WHSV), measured as the grams of benzene per gram of catalyst per hour, is typically greater than about 0.1 h$^{-1}$, and preferably, greater than about 0.3 h$^{-1}$. The benzene WHSV is typically less than about 50 h$^{-1}$, and preferably, less than about 20 h$^{-1}$. The gas hourly space velocity of the ethylene is based on the flow rate of the benzene and the desired molar ratio of benzene to ethylene. From a consideration of the disclosure herein, a skilled artisan will be able to vary the aforementioned alkylation process conditions to accommodate alkylation feedstocks comprising $C_{2-5}$ alkanes other than ethane and $C_{6-12}$ aromatic compounds other than benzene.

The aromatic effluent stream from the alkylation reactor is separated by conventional means to obtain an essentially pure fraction of unconverted $C_{6-12}$ aromatic compound if any, such as benzene, and an essentially pure fraction of $C_{2-5}$ alkyl-substituted aromatic compound, such as ethylbenzene, as well as a corresponding poly($C_{2-5}$ alkyl-substituted) aromatics fraction, such as polyethylbenzenes. Any separation method may be employed which is suitable to the aromatic feed and alkylated aromatic products involved. Preferably and as shown in FIGS. 1 and 2, the separation is conducted in an alkylation products separation unit 57, such as a three column distillation train 58, to recover, for example, benzene in a second benzene column 59, ethylbenzene in a second ethylbenzene column 61, and polyethylbenzenes, including diethylbenzenes and any triethylbenzenes, in a polyethylbenzenes column 63. The unreacted $C_{6-12}$ aromatic compound, for example, benzene, which is recovered, can be recycled via benzene recycle line 49 to the alkylation reactor 53 and/or a transalkylation reactor 71, as described hereinafter. The recovered $C_{2-5}$ alkyl-substituted aromatic compound, for example, ethylbenzene, is recycled via ethylbenzene recycle line 67 to ethylbenzene feed line 5 and thence to the dehydrogenation reactor 9.

The polyalkyl-substituted aromatic compounds which are recovered in the separation of the alkylation effluent stream via separation unit 57, which for example, can be a three column distillation train 58, as described above, including polyethylbenzene column 63, can optionally be fed via polyethylbenzene column overhead line 69 and transalkylator feed line 81 into a transalkylation reactor 71 for transalkylation with $C_{6-12}$ aromatic compound to form the corresponding $C_{2-5}$ alkyl-substituted aromatic compound, thereby increasing the yield of $C_{2-5}$ alkyl-substituted aromatic compound. In a preferred embodiment and as shown in FIGS. 1 and 2, for example, polyethylbenzenes formed in the alkylation reactor 53 and separated in polyethylbenzenes column 63 are fed into the transalkylation reactor 71 with benzene, which is added to gas separator 75 via fresh benzene feed line 77, then to gas separator liquids line 79 and to alkylator feed line 81 to obtain additional ethylbenzene. The transalkylation reactor 71 can have any reactor design and can operate with any catalyst and under any process conditions, provided that the desired $C_{2-5}$ alkyl-substituted aromatic product is produced. A preferred design comprises a conventional fixed bed reactor operating in liquid phase and using any conventional transalkylation catalyst, such as zeolite Y, beta, or mordenite. Transalkylation processes such as these are well known in the art, reference being made again to U.S. Pat. No. 5,476,978. Preferably, the transalkylation catalyst is zeolite Y or beta. For a preferred process involving the transalkylation of benzene with polyethyl-benzenes, the benzene to ethylene molar ratio, calculated in this instance as the total moles of benzenes in the benzene and polyethylbenzenes to total moles of ethylene substituents on the polyethylbenzenes, can suitably range from greater than about 1.8/1, and preferably, greater than about 2.4/1, to less than about 17/1, preferably, less than about 10/1, and more preferably, less than about 5/1. The temperature in the transalkylator is typically greater than about 50° C., preferably, greater than about 120° C., and more preferably, greater than about 180° C. The temperature in the transalkylator is typically less than about 300° C., preferably, less than about 270° C., and more preferably, less than about 240° C. Generally, the pressure in the transalkylator is greater than about 3 psig (21 kPa), preferably, greater than about 100 psig (690 kPa), and more preferably, greater than about 350 psig (2,413 kPa). Generally, the pressure in the transalkylator is less than about 750 psig (5,200 kPa), preferably, less than about 650 psig (4,480 kPa), and more preferably, less than about 500 psig (3,450 kPa). The weight hourly space velocity (WHSV) of the transalkylation feed, measured as the total grams of benzene plus polyethylbenzenes per gram of catalyst per hour, is usually greater than about 0.1 $h^{-1}$, and preferably, greater than about 0.5 $h^{-1}$. The WHSV of the transalkylation feed is usually less than about 50 $h^{-1}$, and preferably, less than about 15 $h^{-1}$. Again, from a consideration of the disclosure herein, the skilled artisan will be able to vary the feed composition and process conditions to accommodate the transalkylation of $C_{6-12}$ aromatic compounds other than benzene with polyalkylated aromatic compounds other than polyethylbenzenes.

Again as shown in FIGS. 1 and 2, the aromatic effluent stream from the transalkylation reactor 71 in transalkylation overhead line 83 is separated by any conventional means in the alkylation products separation unit 57, such as a three column distillation train 58, to recover an essentially pure fraction of unreacted $C_{6-12}$ aromatic compound and an essentially pure fraction of $C_{2-5}$ alkyl-substituted aromatic compound. In a preferred mode of operation, the transalkylation effluent stream in transalkylation overhead line 83 is fed to the three column distillation train 58 used in connection with the alkylation process to recover benzene in a second benzene column 59, ethylbenzene in a second ethylbenzene column 61, polyethylbenzenes in a polyethylbenzenes column 63, and a smaller quantity of residual tar is removed from the bottom of the polyethylbenzenes column via polyethylbenzenes column bottoms line 70. The recovered $C_{6-12}$ aromatic compound, such as benzene from second benzene column 59, is recycled to the alkylation reactor 53 via benzene recycle line 49 and alkylation reactor feed line 51. The recovered $C_{2-5}$ alkyl-substituted aromatic compound, such as ethylbenzene from second ethylbenzene column 61, is recycled via second ethylbenzene column overhead line 67 to ethylbenzene feed line 5 to the dehydrogenation reactor 9 via dehydrogenation reactor feed line 7. The polyalkyl-substituted aromatics fraction, such as polyethylbenzenes from polyethylbenzenes column 63, can be recycled via polyethylbenzenes column overhead line 69 again to the transalkylation reactor 71 through transalkylation reactor feed line 81.

The gaseous vent stream from the alkylation reactor 53, which has been separated from alkylator liquids in gas separator 75 and which comprises predominantly hydrogen, $C_{2-5}$ alkane, and optionally, methane and which typically emerges at high pressure, is taken by gas separator overhead product line 85 and separated, for example, in second separator unit 89 by any known means, such as cryogenic methods or pressure swing absorption methods, into an essentially pure stream of $C_{2-5}$ alkane and an essentially pure stream of hydrogen. The method of separation will depend on the specific alkane component. In a preferred embodiment shown in FIGS. 1 and 2 involving ethane and hydrogen, the gaseous vent steam from the gas separator 75 is taken via gas separator overhead product line 85 to cryocooler 87 and is cryogenically cooled to a temperature less than about −100° C., and more preferably, less than about −140° C.; but preferably, greater than about −180° C., and more preferably, greater than about −165° C., to effect cryogenic separation of hydrogen from ethane. The pressure is preferably greater than about 300 psig (2,068 kPa), and more preferably, greater than about 450 psig (3,103 kPa), but preferably, less than about 800 psig (5,516 kPa), and more preferably, less than about 480 psig (3,310 kPa). The $C_{2-5}$ alkane recovered from the separation in separator 91, is typically obtained in a purity of greater than about 95 mole percent, and preferably, greater than about 99 mole percent. Separator bottoms line 97 containing the purified alkane is recycled to the dehydrogenation reactor 9 via recycled ethane line 3.

Optionally, the hydrogen recovered overhead from separator 91 is fed via separator overhead line 115 to a turboexpander 93 then fed via line 117 to additional separator 95 to recover energy, an essentially pure hydrogen stream which exits additional separator 95 via overhead line 103, and residual $C_{2-5}$ alkane, which exits additional separator 95 via bottoms line 99 for recycle to the dehydrogenation reactor 9 via recycle ethane feed line 3. To effect a high efficiency of separation of ethane from hydrogen, typically, the temperature is decreased to less than about −150° C. The energy recovered can be used for operating the dehydrogenation and/or alkylation unit processes or any other downstream process. The hydrogen which is recovered typically comprises greater than about 95 mole percent purity, and preferably, consists of a commercial grade hydrogen of about 99 mole percent purity. The balance of the hydrogen stream comprises methane. Residual $C_{2-5}$ alkane recovered from the turboexpansion separation is also recycled to the dehydrogenation reactor. Optionally, the hydrogen recovered may be compressed in compressor 101 and sent via hydrogen product line 105 for use elsewhere. As a further option, the cold streams obtained from the second separation unit 89 can be used as auto-refrigerants in the cooling stages of this invention.

The following examples are provided as illustrations of the process of this invention and should not be construed as limiting the invention in any manner. In light of the disclosure herein, those of skill in the art will recognize alternative feeds other than the illustrated ethane and benzene feeds, which can be accommodated by the process of this invention. Also in light of the disclosure herein, those of skill in the art will recognize modifications in the dehydrogenation and alkylation unit processes and unit product separations, which all fall within the scope of this invention.

EXAMPLE 1

An integrated styrene plant of this invention is described which operates for 8,400 hours on stream per year to produce a nominal 350 kilotons annual (KTA) production of styrene.

A concurrent dehydrogenation of ethane and ethylbenzene was conducted in a manner similar to the description in European patent EP-A2-0,905,112. With reference to FIG. 1 and Table 1, dehydrogenation feed stream 7 comprising combined ethylbenzene (0.2 mole fraction) and ethane (0.8 mole fraction) feeds in an ethylbenzene to ethane molar ratio of 0.25/1 was fed to a fluidized bed dehydrogenation reactor 9 operating at essentially atmospheric pressure, 600° C., and a total gas hourly space velocity of 300 h$^{-1}$. The dehydrogenation catalyst comprises gallium oxide (2.33 weight percent), potassium oxide (0.4 weight percent), platinum (75 ppm), silica (1.56 weight percent), the balance to 100 percent being alumina and has a solids residence time in the fluidized bed of 12 minutes. The conversion of ethylbenzene was 55 weight percent, and the selectivity to styrene was 92 weight percent. The conversion of ethane was 10 weight percent, and the selectivity to ethylene was 90 weight percent. Conversion was defined as the weight percentage of raw material which is reacted to form products. Selectivity was defined as the weight percentage of converted raw material which forms the selected product.

The dehydrogenation effluent stream in dehydrogenation overhead line 23, emerging at about 620° C., was cooled in first separator 27 to 40° C. at 5 psig resulting in a condensed aromatics stream. The overhead vapor stream containing hydrogen, ethane, ethylene, methane, and uncondensed aromatics was compressed in compressor 29 to 465 psig (3,200 kPa) and further cooled to 10° C., and fed to a second separator 31 to recover additional aromatics, up to a total of 99 weight percent aromatics recovery. The first condensed aromatic stream in aromatics effluent line 33 and second separator bottoms line 38, respectively, were combined as raw liquid product in line 33, comprising essentially ethylbenzene and styrene. The raw liquid product was degassed and fed to conventional product separation three column distillation train 37 to recover recycle unconverted ethylbenzene in ethylbenzene column 43 and finished styrene product in styrene column 45. A smaller amount of byproducts comprising benzene and toluene was recovered from benzene column 39 via benzene line 41, and heavies or tar were recovered from the bottoms of the styrene column 45 in tar line 47.

A high pressure gas stream derived from the secondary aromatics recovery step of second separator 31, mentioned hereinabove, and comprising predominantly ethane, ethylene, and hydrogen ("dilute ethylene stream") was fed via essentially non-aromatics overhead gas line 35 to an alkylation reactor 53 for ethylbenzene production. The alkylation was conducted in a manner similar to that described in WO 98/09929. The alkylation reactor 53 consists of a catalytic distillation reactor loaded with zeolite β(beta) (PQ Corporation) and operating in mixed gas-liquid phase mode. The dilute ethylene stream in essentially non-aromatics overhead gas line 35 and benzene from recycle benzene feed line 49 are combined in alkylation feed line 51 and fed to the alkylation reactor 53. Additionally, fresh benzene was fed to the alkylation reactor via fresh benzene feedline 77 by way of gas separator liquid line 79 and alkylator feed line 78. The total feeds into alkylation reactor 53 contain equimolar concentrations of benzene and ethylene. The alkylation process operates at 280° C., 465 psig (3,204 kPa), and a benzene weight hourly space velocity of 0.7 h$^{-1}$. The conversion of benzene was essentially 100 percent. About 90 percent of the ethylene was reacted in the alkylator to produce an aromatics effluent stream via alkylation reactor bottoms line 55, which was fed to conventional three column distillation train 58 to recover any unreacted benzene in second benzene column 59, ethylbenzene in second ethylbenzene column 61 and polyethylbenzenes in polyethylbenzene column 63. Recovered benzene can be recycled to the alkylation reactor via benzene recycle line 49. Internal to the alkylation process some polyethylbenzenes, including diethylbenzenes and some triethylbenzenes, were also produced, which were fed to a transalkylation reactor 71 operating in a manner similar to that described in U.S. Pat. No. 5,476,978. The transalkylation reactor 71 consists of a fixed bed reactor operating in liquid phase mode. The polyethylbenzenes are contacted with benzene in the transalkylator in the presence of zeolite Y catalyst (UOP LZY-82 zeolite Y). The transalkylator operates at 210° C., 450 psig (3,103 kPa), a benzene to ethylene molar ratio of 2.75/1, and a polyethylbenzenes fraction weight hourly space velocity of 1.8h$^{-1}$. The transalkylation produces additional ethylbenzene, the total ethylbenzenes from the alkylation/transalkylation being represented by second ethylbenzene column overhead line 67. The ethylbenzene stream in second ethylbenzene column overhead line 67 was recycled via ethylbenzene feed line 5 to the dehydrogenation reactor 9. Any polyethylbenzenes which are not back reacted to ethylbenzene were removed as heavies, as shown in polyethylbenzene bottoms line 70. This stream also contains any entrained aromatic species other than benzene and ethylbenzene, which may enter with the gaseous feed and be subsequently alkylated.

The off-gas from the alkylation reactor 53 in gas separator overhead product line 85 at 465 psig (3,204 kPa) was fed to the second separation unit 89 operating at a minimum temperature of −155° C. to separate hydrogen in hydrogen product line 105 and ethane in recycled ethane feed line 3. The hydrogen stream was exhausted at 10 psig (69 kPa) for recovery of energy. Refer to Table 1 for the hydrogen stream in line 105 and recycle ethane stream in line 3. The cryogenic system was operated such as to minimize the amount of methane contained in the recycle ethane stream. Energy (520 kilowatts) was recovered in the turboexpander unit 93 from the process.

TABLE 1

Integrated Process of Preparing Styrene from Benzene and Ethane:
Unit Operations Feed and Product Streams

| Stream or line (wt percent) | 7 | 23 | 35 | 33 | 51 | 85 | 67 | 70 | 3 | 105 |
|---|---|---|---|---|---|---|---|---|---|---|
| Ethane | 60.86 | 55.02 | 89.13 | 1.68 | 58.42 | 97.89 | 0.00 | 0.00 | 99.20 | 2.30 |
| Ethylbenzene | 38.70 | 18.64 | 0.07 | 47.69 | 0.05 | 0.00 | 99.80 | 0.00 | 0.00 | 0.00 |

TABLE 1-continued

Integrated Process of Preparing Styrene from Benzene and Ethane:
Unit Operations Feed and Product Streams

| Stream or line (wt percent) | 7 | 23 | 35 | 33 | 51 | 85 | 67 | 70 | 3 | 105 |
|---|---|---|---|---|---|---|---|---|---|---|
| Ethylene | 0.22 | 5.59 | 9.09 | 0.12 | 5.96 | 0.40 | 0.00 | 0.00 | 0.40 | 0.10 |
| Styrene | 0.00 | 18.52 | 0.02 | 47.45 | 0.02 | 0.00 | 0.00 | 0.00 | 0.00 | 0.00 |
| Methane | 0.15 | 0.19 | 0.31 | Trace | 0.20 | 0.34 | 0.00 | 0.00 | 0.28 | 4.34 |
| Benzene | 0.00 | 0.32 | 0.13 | 0.63 | 34.52 | 0.00 | 0.10 | 0.00 | 0.00 | 0.00 |
| Toluene | 0.00 | 0.20 | 0.01 | 0.49 | 0.01 | 0.00 | 0.10 | 0.00 | 0.00 | 0.00 |
| Xylenes | 0.00 | 0.07 | Trace | 0.19 | Trace | 0.00 | 0.00 | 0.00 | 0.00 | 0.00 |
| Hydrogen | 0.06 | 0.76 | 1.25 | Trace | 0.82 | 1.37 | 0.00 | 0.00 | 0.11 | 93.26 |
| Heavies | 0.00 | 0.68 | 0.00 | 1.74 | 0.00 | 0.00 | 0.00 | 100.00 | 0.00 | 0.00 |
| Flow (kg/h) | 222,309 | 222,309 | 135,601 | 86,708 | 206,867 | 123459 | 44775 | 135 | 121787 | 1,670 |

EXAMPLE 2

An integrated styrene plant of this invention was described, the plant operating for 8400 hours on stream per year to produce a nominal 350 KTA of styrene product. This example was similar to Example 1, with the following exceptions, as shown in FIG. 2. The essentially non-aromatic gaseous stream obtained from the dehydrogenation reactor 9 was passed through a rough cut $C_2$ splitter tower 107 to enrich the essentially non-aromatics overhead gas stream in ethylene, and the alkylation reactor 53 was therefore operated in full gas phase using zeolite ZSM-5 catalyst.

A concurrent dehydrogenation of ethane and ethylbenzene was conducted in a manner similar to the description in European patent EP-A2-0,905,112. With reference to FIG. 2 and Table 2, dehydrogenation reactor feed line 7 comprising combined ethylbenzene (0.2 mole fraction) and ethane (0.8 mole fraction) feeds in an ethylbenzene to ethane molar ratio of 0.25/1 was fed to a fluidized bed dehydrogenation reactor 9 operating at essentially atmospheric pressure, 600° C., and a total gas hourly space velocity of 300 h$^{-1}$. The dehydrogenation catalyst comprises gallium oxide (2.33 weight percent), potassium oxide (0.4 weight percent), platinum (75 ppm), silica (1.56 weight percent), the balance to 100 percent being alumina and has a solids residence time in the fluidized bed of 12 minutes. The conversion of ethylbenzene is 55 weight percent, and the selectivity to styrene was 92 weight percent. The conversion of ethane was 10 weight percent, and the selectivity to ethylene was 90 weight percent.

The dehydrogenation effluent stream in dehydrogenation effluent line 23, emerging at about 620° C., was cooled to 40° C. at 5 psig in first separator 27 resulting in a condensed aromatics stream which exits the first separator via aromatics effluent line 33. The overhead vapor stream containing hydrogen, ethane, ethylene, methane, and uncondensed aromatics was compressed in compressor 29 to 465 psig (3,200 kPa) and further cooled to 10° C., and then fed to a secondary separator in a manner similar to first separator 27 (reiteration) to recover additional aromatics, up to a total of 99 weight percent aromatics recovery. The first and second condensed aromatic streams from aromatics effluent line 33 and an auxiliary separator (not shown in FIG. 2) were combined as raw liquid product in aromatics effluent line 33, comprising essentially ethylbenzene and styrene. The raw liquid product in aromatics effluent line 33 was degassed and fed to conventional product separation three column distillation train 37 to recover recycle unconverted ethylbenzene in ethylbenzene column 43, finished styrene product in styrene column 45, a smaller amount of byproducts comprising benzene and toluene from benzene column 39, and heavies from styrene column out the bottoms in tar line 47.

The non-aromatic gaseous stream obtained from the last stage of compression in compressor 29 was fed to a rough cut $C_2$ alkene-alkane splitter tower 107 using a propylene refrigeration condenser 119 (–27° C.) and reflux or drip drum 109 to produce gaseous product via essentially non-aromatics overhead gas line 35 that was the ethylene feed to the alkylation unit 53. The ethylene feed via alkylation reactor feed line 51 comprises 48.8 weight percent ethylene. The bottoms product from the rough cut $C_2$ alkene-alkane splitter tower 107 via splitter tower bottoms line 111 is rich in ethane (98.9 percent) and depleted of ethylene. This ethane rich stream was combined with recycle ethane feed line 3 and fed as an ethane recycle stream to the dehydrogenation reactor 9.

An alkylation feed comprising benzene from fresh benzene feed line 77, transported through gas separator liquid line 79 to alkylator feed line 78, and recycle benzene via benzene recycle line 49, and the enriched ethylene stream, containing ethylene, hydrogen, and ethane in essentially non-aromatics overhead gas line 35, was fed into an alkylation unit 53. The ethylene stream and recycle benzene were combined in alkylation reactor feed line 51. Fresh benzene was added via alkylator feed line 78. The alkylation reactor 53 was operated in full gas phase using a zeolite ZSM-5 catalyst. The benzene to ethylene molar ratio was 4.23/1. The alkylation process operates at 400° C., 369 psig (2,545 kPa) and total feed weight hourly space velocity of 130 h$^{-1}$. Essentially all of the ethylene was reacted in the alkylation reactor 53. The benzene conversion was 22 percent. The selectivity to ethylbenzene was 92 mole percent, and the total selectivity to ethylbenzene and polyethylbenzenes was 98.8 percent. The effluent from the alkylator was fed via alkylation bottoms line 55 to conventional three column distillation train 58 to recover unreacted benzene in second benzene column 59, ethylbenzene in second ethylbenzene column 61, and polyethylbenzenes in polyethylbenzene column 63. The polyethylbenzenes were recovered as additional ethylbenzene by the use of a transalkylation step in transalkylation reactor 71, similar to Example 1. The ethylbenzene stream from second ethylbenzene column overhead line 67 was recycled to the dehydrogenation reactor 9 via ethylbenzene recycle line 5. Those alkylated products which are not reacted back to product ethylbenzene were removed as heavies from the polyethylbenzene column 63 via polyethylbenzene bottoms line 70, which also contains any entrained aromatic species other than benzene and ethylbenzene that may enter with the gaseous feed and be subsequently alkylated.

The off-gas from the alkylation unit in gas separator overhead product line 85, at 465 psig (3,204 kPa) was fed to the second separation unit 89, consisting of cryo-cooler 87, alkylation separator 91, turboexpander 93, and additional alkylation separator 95, operating at a minimum temperature of −155° C. to separate hydrogen and ethane. The hydrogen stream was exhausted at 10 psig (69 kPa) for recovery of energy. Refer to the hydrogen stream in hydrogen product line 105 (Table 2) and recycle ethane stream from separator bottoms lines 97 and 99, respectively, which were combined into recycle ethane feed line 3 (Table 2). The cryogenic system was operated such as to minimize the amount of methane contained in the recycle ethane stream. Energy (520 kilowatts) was recovered in the turboexpander 93 from the process.

TABLE 2

Integrated Process of Preparing Styrene from Benzene and Ethane:
Unit Operations Feed and Product Streams

| Stream or line (wt percent) | 7 | 23 | 35 | 33 | 51 | 85 | 67 | 70 | 3 | 105 | 49 + 78 | 111 |
|---|---|---|---|---|---|---|---|---|---|---|---|---|
| Ethane | 60.86 | 54.98 | 43.59 | 0.88 | 5.65 | 85.21 | 0.00 | 0.00 | 98.93 | 0.15 | 0.00 | 98.90 |
| Ethylbenzene | 38.91 | 18.63 | 0.00 | 47.89 | 0.00 | 0.00 | 100.0 | 0.00 | 0.00 | 0.00 | 0.00 | 0.35 |
| Ethylene | 0.00 | 5.58 | 48.84 | 0.06 | 6.33 | 0.00 | 0.00 | 0.00 | 0.00 | 0.00 | 0.00 | 0.25 |
| Styrene | 0.00 | 18.51 | 0.00 | 47.87 | 0.00 | 0.00 | 0.00 | 0.00 | 0.00 | 0.00 | 0.00 | 0.13 |
| Methane | 0.05 | 0.08 | 0.73 | 0.00 | 0.09 | 1.43 | 0.00 | 0.00 | 0.99 | 4.17 | 0.00 | 0.00 |
| Benzene | 0.17 | 0.49 | 0.00 | 0.84 | 87.04 | 0.00 | 0.00 | 0.00 | 0.00 | 0.00 | 100.0 | 0.34 |
| Toluene | 0.02 | 0.21 | 0.00 | 0.52 | 0.00 | 0.00 | 0.00 | 0.00 | 0.00 | 0.00 | 0.00 | 0.03 |
| Xylenes | Trace | 0.07 | 0.00 | 0.19 | 0.00 | 0.00 | 0.00 | 0.00 | 0.00 | 0.00 | 0.00 | 0.00 |
| Hydrogen | 0.00 | 0.76 | 6.84 | 0.00 | 0.89 | 13.36 | 0.00 | 0.00 | 0.08 | 95.69 | 0.00 | 0.00 |
| Heavies | 0.00 | 0.68 | 0.00 | 1.76 | 0.00 | 0.00 | 0.00 | 100.00 | 0.00 | 0.00 | 0.00 | 0.00 |
| Flow (kg/h) | 222484 | 222484 | 24752 | 85728 | 190939 | 12663 | 44720 | 425 | 10904 | 1759 | 132955 | 112004 |

The data in Tables 1 and 2 illustrate the high selectivity of the dehydrogenation reaction to ethylene and styrene, the high degree of purity of the ethylene stream, the high selectivity of the alkylation/-transalkylation reaction to ethylbenzene (99.7 weight percent selectivity to ethylbenzene having a purity of 99.8 weight percent), the high efficiency of the ethane-hydrogen separation, and the high degree of purity of the hydrogen produced. The aromatic compounds in aromatics effluent line 33, containing crude styrene, are readily separated into high purity styrene, recycle ethylbenzene, and some by-product aromatics, specifically benzene, toluene, and xylenes. An overall aromatics recovery of 99 weight percent was achieved.

What is claimed is:

1. An integrated process of preparing a $C_{2-5}$ alkenyl-substituted aromatic compound and hydrogen from a $C_{2-5}$ alkane and a $C_{6-12}$ aromatic compound, the process comprising:

(a) contacting a $C_{2-5}$ alkane and a $C_{2-5}$ alkyl-substituted aromatic compound in a dehydrogenation reactor in the presence of a dehydrogenation catalyst under process conditions sufficient to prepare a dehydrogenation effluent stream comprising a $C_{2-5}$ alkenyl-substituted aromatic compound, the $C_{2-5}$ alkyl-substituted aromatic compound, a $C_{2-5}$ alkene, the $C_{2-5}$ alkane, and hydrogen;

(b) separating the dehydrogenation effluent stream under conditions sufficient to obtain an essentially non-aromatic, gaseous stream comprising the $C_{2-5}$ alkene, the $C_{2-5}$ alkane, and hydrogen, and an aromatics stream comprising the $C_{2-5}$ alkenyl-substituted aromatic compound and the $C_{2-5}$ alkyl-substituted aromatic compound, the aromatics recovery being greater than about 90 weight percent;

(c) feeding the essentially non-aromatic gaseous stream comprising $C_{2-5}$ alkene, $C_{2-5}$ alkane, and hydrogen into an alkylation reactor wherein the gaseous stream is contacted with a $C_{6-12}$ aromatic compound in the presence of an alkylation catalyst under process conditions sufficient to prepare an alkylation effluent stream comprising the $C_{2-5}$ alkyl-substituted aromatic compound, and optionally, poly($C_{2-5}$ alkyl-substituted) aromatic compounds(s), and optionally, unreacted $C_{6-12}$ aromatic compound, and a gaseous stream comprising $C_{2-5}$ alkane and hydrogen;

(d) separating the alkylation effluent stream under conditions sufficient to recover a $C_{2-5}$ alkyl-substituted aromatic compound fraction, and optionally, a poly($C_{2-5}$ alkyl-substituted) aromatic compound(s) fraction, and optionally, a $C_{6-12}$ aromatic compound fraction;

(e) recycling the $C_{2-5}$ alkyl-substituted aromatic compound recovered from steps (b) and (d) into the dehydrogenation reactor of step (a);

(f) separating the gaseous stream comprising $C_{2-5}$ alkane and hydrogen obtained from step (c) under conditions sufficient to obtain an essentially pure stream of hydrogen and an essentially pure stream of $C_{2-5}$ alkane; and (g) recycling the $C_{2-5}$ alkane from step (f) into the dehydrogenation reactor of step (a).

2. The process of claim 1 wherein the $C_{2-5}$ alkane is selected from the group consisting of ethane, propane, and butanes.

3. The process of claim 2 wherein the $C_{2-5}$ alkane is ethane.

4. The process of claim 1 wherein the $C_{6-12}$ aromatic compound is represented by the formula:

wherein n is an integer from 0 to about 3, and wherein each $R^1$ is independently selected from the group consisting of hydrogen and $C_{1-5}$ alkyl moieties, with the balance of the 6-n bonds being to hydrogen.

5. The process of claim 4 wherein the $C_{6-12}$ aromatic compound is benzene.

6. The process of claim 1 wherein the $C_{2-5}$ alkyl-substituted aromatic compound is represented by the formula:

wherein n is an integer from 0 to about 3; each $R^1$ is independently selected from the group consisting of hydrogen and $C_{1-5}$ alkyl moieties; and $R^2$ is a $C_{2-5}$ alkyl moiety, with the balance of the 5-n bonds being to hydrogen.

7. The process of claim 1 wherein the $C_{2-5}$ alkyl-substituted aromatic compound is selected from the group consisting of ethylbenzene, ethyltoluene, diethylbenzene, isopropylbenzene, and di(isopropyl)benzene.

8. The process of claim 1 wherein the dehydrogenation reactor comprises a fluidized bed reactor.

9. The process of claim 1 wherein the dehydrogenation catalyst comprises gallium, a platinum group metal, or combinations thereof, supported on alumina or mordenite zeolite.

10. The process of claim 9 wherein the dehydrogenation catalyst comprises gallium supported on alumina in the delta or theta phase, or in a mixture of delta plus theta phases, or theta plus alpha phases, or delta plus theta plus alpha phases, modified with silica, and having a surface area of less than about 100 $m^2/g$.

11. The process of claim 10 wherein the dehydrogenation catalyst comprises:
  (i) from about 0.1 to about 34 percent by weight of gallium oxide ($Ga_2O_3$);
  (ii) from about 1 to about 99 parts per million (ppm) by weight of platinum;
  (iii) from about 0.05 to about 5 percent by weight of an alkaline and/or alkaline-earth oxide;
  (iv) from about 0.08 to about 3 percent by weight silica;
  (v) the balance to 100 percent being alumina.

12. The process of claim 1 wherein the dehydrogenation catalyst comprises:
  i) from about 6 to about 30 percent by weight of chromium oxide ($Cr_2O_3$);
  ii) from about 0.1 to about 3.5 percent by weight stannous oxide (SnO);
  iii) from about 0.4 to about 3 percent by weight of an alkaline oxide;
  iv) from about 0.08 to about 3 percent by weight silica;
  v) the balance to 100 percent being alumina in the delta or theta phase, or a mixture of delta plus theta phases, or theta plus alpha phases, or delta plus theta plus alpha phases.

13. The process of claim 1 wherein the dehydrogenation catalyst comprises:
  (i) from about 1 to about 60 percent by weight iron oxide;
  (ii) from about 0.1 to about 20 percent by weight of at least one alkaline or alkaline earth metal oxide;
  (iii) from about 0 to about 15 percent by weight of at least one rare earth oxide;
  (iv) the complement to 100 percent being a carrier consisting of a microspheroidal alumina with a diameter selected from those in delta or theta phase, or in a mixture of theta plus alpha phases, or in a mixture of delta plus theta plus alpha phases, modified with from about 0.08 to about 5.0 weight percent of silica.

14. The process of claim 13 wherein the carrier has an average particle diameter and particle density such that the final product can be classified as Group-A by Geldart and a surface area of less than about 150 $m^2/g$.

15. The process of claim 13 wherein the alkaline oxide is potassium oxide.

16. The process of claim 13 wherein the rare earth oxide is selected from the group consisting of cerium oxide, lanthanum oxide, praseodymium oxide, and mixtures thereof.

17. The process of claim 1 wherein the dehydrogenation is conducted at a temperature greater than about 450° C. and less than about 700° C.

18. The process of claim 1 wherein the dehydrogenation is conducted at a pressure greater than about 0.1 atm absolute (10 kPa) and less than about 3.0 atm absolute (300 kPa).

19. The process of claim 1 wherein the dehydrogenation is conducted at a molar ratio of $C_{2-5}$ alkyl-substituted aromatic compound to $C_{2-5}$ alkane in the range from about 0.01/1 to about 1/1.

20. The process of claim 1 wherein the dehydrogenation is conducted at a gas hourly space velocity greater than about 100 $h^{-1}$ and less than about 10,000 $h^{-1}$.

21. The process of claim 1 wherein a portion of the dehydrogenation catalyst is continuously cycled to a regenerator for regeneration and then a portion of the regenerated catalyst is returned to the dehydrogenation reactor.

22. The process of claim 21 wherein the regeneration comprises contacting the catalyst with oxygen, and optionally, a gaseous fuel.

23. The process of claim 22 wherein the gaseous fuel is selected from the group consisting of methane, ethane, fuel gas, and mixtures thereof.

24. The process of claim 21 wherein the regeneration is conducted at a temperature between about 600° C. and about 700° C.

25. The process of claim 1 wherein the step (b) separation comprises cooling and compression stages, which may be reiterated one or more times.

26. The process of claim 25 wherein in step (b) a first separator is employed at a temperature less than about 50° C. and greater than about 30° C. and at a pressure greater than about 0.5 psig (3.5 kPa) and less than about 50 psig (345 kPa).

27. The process of claim 26 wherein in step (b) a compressor is employed after the first separator, and the compressor operates at a pressure greater than about 300 psig (2,069 kPa) and less than about 600 psig (4,137 kPa).

28. The process of claim 27 wherein in step (b) a second separator is employed after the compressor, the second separator operating at a temperature less than about 20° C. and greater than about 0° C.

29. The process of claim 25 wherein the aromatics stream obtained from the separation of step (b) is separated in a distillation train into an essentially pure stream of $C_{2-5}$ alkenyl-substituted aromatic compound and an essentially pure stream of $C_{2-5}$ alkyl-substituted aromatic compound.

30. The process of claim 25 wherein the total aromatics recovery is greater than about 95 weight percent.

31. The process of claim 25 wherein the total aromatics recovery is greater than about 99 weight percent.

32. The process of claim 1 wherein the essentially non-aromatic, gaseous stream from step (b) containing $C_{2-5}$ alkane, $C_{2-5}$ alkene, and hydrogen comprises from greater than about 1 to less than about 40 mole percent alkene.

33. The process of claim 1 wherein the essentially non-aromatic, gaseous stream from step (b) containing $C_{2-5}$ alkane, $C_{2-5}$ alkene, and hydrogen is fed to a splitter tower to enrich the stream in $C_{2-5}$ alkene.

34. The process of claim 33 wherein the splitter tower employs a refrigeration condenser using propylene refrigeration.

35. The process of claim 33 wherein the essentially non-aromatic gaseous stream from the splitter tower has an alkene concentration of greater than about 40 and less than about 70 mole percent.

36. The process of claim 1 wherein the alkylation reactor is a catalytic distillation reactor or a fixed bed reactor.

37. The process of claim 1 wherein the alkylation catalyst is selected from the group consisting of crystalline porous solids with structure codes MFI, MWW, FAU, BEA, LTL, MAZ, LTA, MOR, ESV, OFF, and crystalline porous solids MCM-22, MCM-36, MCM-49, MCM-56, and ERS-10.

38. The process of claim 37 wherein the alkylation is conducted in mixed gas-liquid phases, and the alkylation catalyst is selected from zeolites beta, mordenite, Y, omega, L, X and A and MCM-22.

39. The process of claim 1 wherein the alkylation is conducted in a gas phase, and the alkylation catalyst is ZSM-5.

40. The process of claim 1 wherein the alkylation is conducted at a molar ratio of $C_{6-12}$ aromatic compound to $C_{2-5}$ alkene, in a reaction zone, of greater than about 1.8/1 and less than about 100/1.

41. The process of claim 1 wherein the alkylation is conducted at a temperature greater than about 50° C. and less than about 450° C.

42. The process of claim 1 wherein the alkylation is conducted at a pressure greater than about 3 psig (21 kPa) and less than about 750 psig (5,171 kPa).

43. The process of claim 1 wherein the weight hourly space velocity of the benzene is greater than about 0.1 $h^{-1}$ and less than about 50 $h^{-1}$.

44. The process of claim 1 wherein an alkylation effluent stream obtained from the alkylation reactor is separated in a distillation train.

45. The process of claim 1 wherein $C_{6-12}$ aromatic compound recovered from the separation (d) of the alkylation effluent stream is recycled to the alkylation reactor.

46. The process of claim 1 wherein poly($C_{2-5}$ alkyl-substituted) aromatic compound(s) recovered from the separation step (d) are fed to a transalkylation reactor wherein they are contacted with $C_{6-12}$ aromatic compound in the presence of a transalkylation catalyst to produce $C_{2-5}$ alkyl-substituted aromatic compound.

47. The process of claim 46 wherein the transalkylation catalyst is selected from zeolites mordenite, beta, and Y.

48. The process of claim 46 wherein the transalkylation reactor is a fixed bed reactor operating at a temperature greater than about 50° C. and less than about 300° C.

49. The process of claim 46 wherein the $C_{6-12}$ aromatic compound is benzene; the poly($C_{2-5}$ alkyl substituted) benzenes are polyethylbenzenes; and the ratio of the total moles of benzenes in the benzene and polyethylbenzenes to moles of ethyl groups on the polyethylbenzenes is greater than about 1.8/1 and less than about 17/1.

50. The process of claim 46 wherein the transalkylation reactor is operated at a pressure greater than about 3 psig (21 kPa) and less than about 750 psig (5,200 kPa).

51. The process of claim 46 wherein the transalkylation reactor is operated at a weight hourly space velocity of the total feed, including benzene and polyethylbenzenes, of greater than about 0.1 $h^{-1}$ and less than about 50 $h^{-1}$.

52. The process of claim 1 wherein a cryogenic separator is used to separate the stream of hydrogen and $C_{2-5}$ alkane in step (f).

53. The process of claim 52 wherein the cryogenic separation is conducted at a temperature greater than about −180° C. and less than about −100° C.

54. The process of claim 1 wherein the hydrogen recovered from step (f) is fed to a turboexpander so as to produce an essentially pure stream of hydrogen and to recover energy.

55. The process of claim 54 wherein the hydrogen recovered is at least about 99 percent pure.

56. The process of claim 52 or 54 wherein a cold stream obtained from the separation step using cryogenic cooling or turboexpansion is used as an auto-refrigerant.

57. An integrated process of preparing styrene from benzene and ethane comprising:
 (a) contacting ethane and ethylbenzene in a dehydrogenation reactor in the presence of a dehydrogenation catalyst under process conditions sufficient to prepare a dehydrogenation effluent stream comprising styrene, ethylbenzene, ethane, ethylene, and hydrogen;
 (b) separating the dehydrogenation effluent stream under conditions sufficient to obtain an essentially non-aromatic gaseous stream comprising ethylene, ethane, and hydrogen, and an aromatics stream comprising ethylbenzene and styrene, the total aromatics recovery being greater than about 90 weight percent;
 (c) feeding the essentially non-aromatic gaseous stream comprising ethylene, ethane, and hydrogen into an alkylation reactor wherein the stream is contacted with benzene in the presence of an alkylation catalyst under process conditions sufficient to prepare an alkylation effluent stream comprising ethylbenzene and, optionally, poly(ethyl)benzenes and unreacted benzene, and an essentially non-aromatic gaseous stream comprising ethane and hydrogen;
 (d) separating the alkylation effluent stream under conditions sufficient to recover ethylbenzene and, optionally, polyethylbenzenes and benzene;
 (e) recycling the ethylbenzene recovered from steps (b) and (d) into the dehydrogenation reactor of step (a);
 (f) separating the essentially non-aromatic, gaseous stream comprising ethane and hydrogen obtained from step (c) under conditions sufficient to obtain an essentially pure stream of hydrogen and an essentially pure stream of ethane; and
 (g) recycling the ethane from step (f) into the dehydrogenation reactor of step (a).

58. The process of claim 57 wherein the dehydrogenation reactor is a fluidized bed reactor employing a dehydrogenation catalyst selected from the group consisting of gallium oxide catalysts, optionally containing platinum; chromium oxide catalysts, optionally containing tin; and iron oxide catalysts; the catalysts optionally containing an additional metal selected from the alkaline, alkaline earth, and rare earth metals, and mixtures thereof; the catalysts optionally being supported on silica or alumina.

59. The process of claim 57 wherein the essentially non-aromatic gaseous stream obtained from the dehydrogenation step and containing ethylene, hydrogen, and ethane is fed to a $C_2$ splitter to enrich the stream in ethylene.

60. The process of claim 57 wherein the alkylation reactor is operated in gas phase using a zeolite ZSM-5 catalyst.

61. The process of claim 57 wherein the alkylation reactor is a catalytic distillation reactor operating in mixed gas-liquid phase mode using an alkylation catalyst selected from the group consisting of zeolites beta, Y, mordenite, and MCM-22.

62. The process of claim 57 wherein the ethane and hydrogen stream obtained from the alkylation step is separated using cryogenic cooling and compression, and optionally, a turboexpander.

63. The process of claim 57 wherein the total aromatics recovery is greater than about 95 weight percent, and the hydrogen recovered is essentially 99 mole percent purity.

* * * * *